United States Patent
Kim

(10) Patent No.: US 7,416,886 B2
(45) Date of Patent: Aug. 26, 2008

(54) PORCINE UROPLAKIN II PROMOTER AND THE PRODUCTION METHOD OF USEFUL PROTEINS USING SAID PROMOTER

(75) Inventor: Jin-Hoi Kim, Kyeongsangnam-do (KR)

(73) Assignee: Cho-A Pharm Co., Ltd., Seoul (KR)

( * ) Notice: Subject to any disclaimer, the term of this patent is extended or adjusted under 35 U.S.C. 154(b) by 217 days.

(21) Appl. No.: 10/532,580

(22) PCT Filed: Nov. 4, 2003

(86) PCT No.: PCT/KR03/02339

§ 371 (c)(1),
(2), (4) Date: Apr. 25, 2005

(87) PCT Pub. No.: WO2004/042062

PCT Pub. Date: May 21, 2004

(65) Prior Publication Data

US 2006/0236412 A1    Oct. 19, 2006

(30) Foreign Application Priority Data

Nov. 4, 2002   (KR) .................. 10-2002-0067856
Nov. 3, 2003   (KR) .................. 10-2003-0077256

(51) Int. Cl.
*C12N 15/63*   (2006.01)
*C12N 15/11*   (2006.01)
*C12N 15/85*   (2006.01)
*C07H 21/04*   (2006.01)
*A01K 67/00*   (2006.01)
*C07K 1/70*   (2006.01)

(52) U.S. Cl. .................. 435/325; 536/23.1; 536/24.1; 435/325; 800/4; 800/8; 800/21

(58) Field of Classification Search ........... None
See application file for complete search history.

(56) References Cited

U.S. PATENT DOCUMENTS 6,001,646 A    12/1999   Sun
6,339,183 B1    1/2002   Sun

2002/0092033 A1    7/2002   Sun

OTHER PUBLICATIONS

Kwon et al (Cloning, Sequencing and Expression Analysis of the Porcine uroplakin II gene, Biochemical and Biophysical Research Communications, 2002. 293:862-869).*
Zbikowska et al (The use of the uromodulin promoter to target production of recombinant proteins into urine of transgenic animals, Transgenic Research, 2002. 11:425-435).*
Kwon et al (Cloning and Molecular Dissection of the 8.8 kb Pig Uroplakin II Promoter Using Transgenic Mice and RT4 cells, Journal of Cellular Biochemistry, 2006. 99:462-477).*
Robl et al (Transgenic animal production and animal biotechnology, Theriogenology, 2007. 67:127-133).*
D. N. Kwon et al., "Cloning, sequencing, and expression analysis of the porcine uroplakin II gene," Biochemistry and Biophysical Research Communication, vol. 293, No. 2, pp. 862-869 (2002).
NCBI GeneBank Association No. AY044189, 4 pages including one sequence listing, (2001).
Takahito Inoue et al., "Position-independent human β-globin gene expression mediated by a recombinant adeno-associated virus vector carrying the chicken β-globin insulator," J. Hum Genet, vol. 44, No. 3, pp. 152-162 (1999).
Romain Zufferey et al., "Woodchuck Hepatitis Virus Post-transcriptional Regulatory Element Enhances Expression of Transgenes Delivered by Retroviral Vectors," Journal of Virology, vol. 73, No. 4, pp. 2886-2892 (1999).
Lin et al., "Cloning and expression of the human erythropoietin gene," Proc. Natl. Acad. Sci USA, 82:7580-7584 (1985).

* cited by examiner

*Primary Examiner*—Janet L. Epps-Ford
(74) *Attorney, Agent, or Firm*—Greenblum & Bernstein, P.L.C.

(57) ABSTRACT

The present invention relates to a porcine uroplakin II gene promoter, an expression vector containing the promoter, and a method for producing useful proteins using the vector. The promoter of the present invention promotes the bladder-specific expression of a target protein at high efficiency. An animal, which was transformed using the inventive promoter so as to express the target protein, secretes the target protein in its urine at high concentration, and the protein thus produced shows a superior physiological activity to that of the same kind of the existing protein. As a result, the inventive promoter, the expression vector and transgenic animal using the promoter, can be advantageously used in the production field of useful proteins that are medicinally valuable.

22 Claims, 7 Drawing Sheets

[FIG. 1]
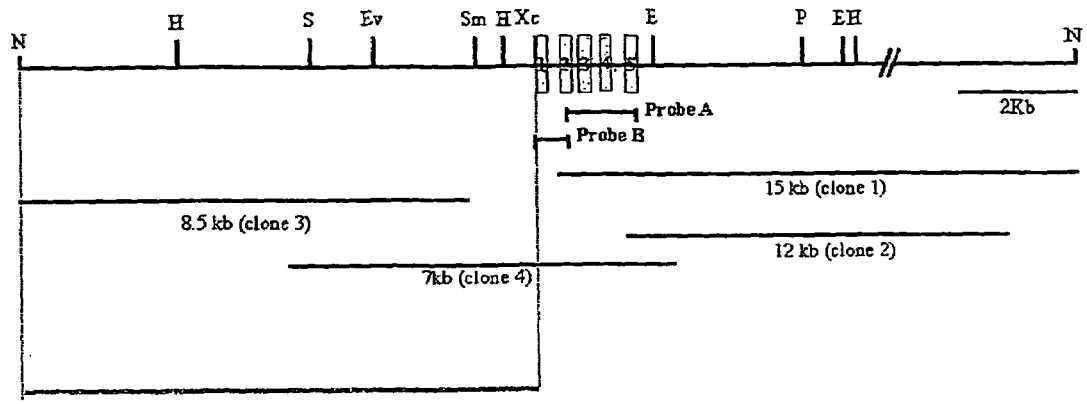
Porcine UPII promoter : 8847kb
[FIG. 2]
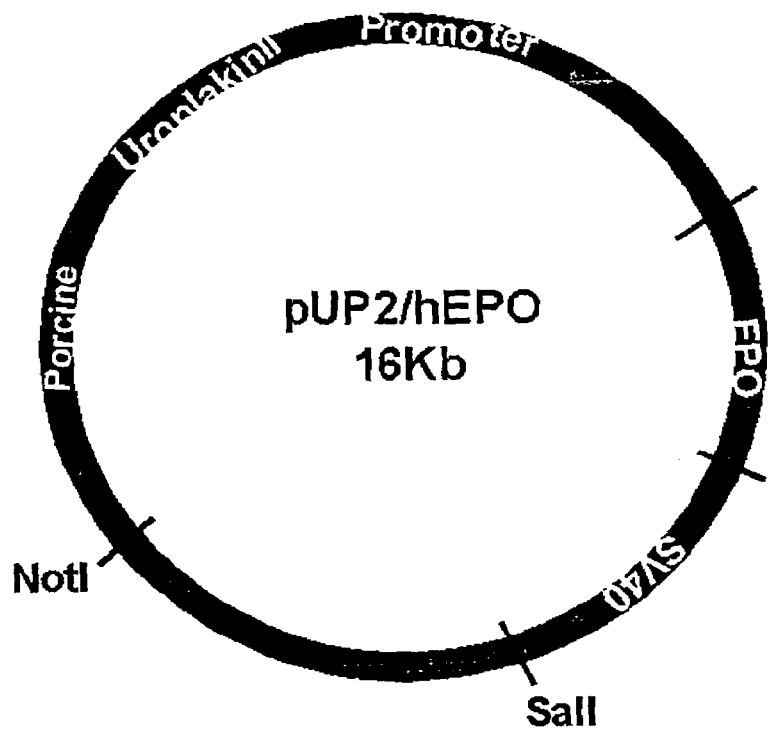
pUP2/hEPO Expression Vector

[FIG. 3]
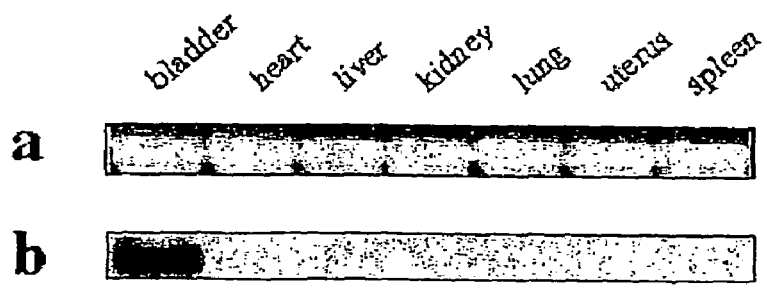
[FIG. 4]
a
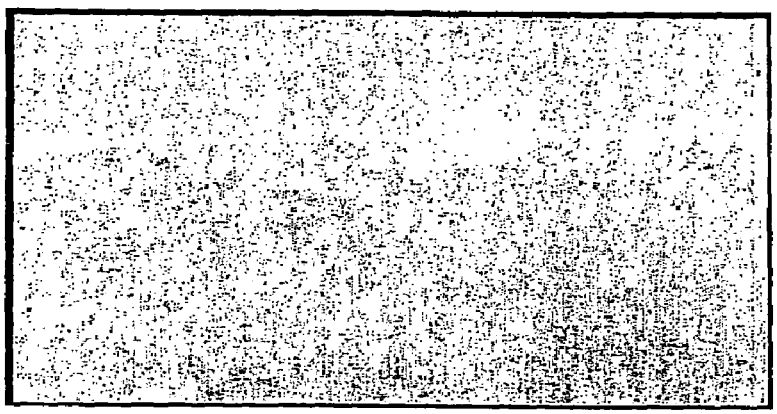
b

[FIG. 5]
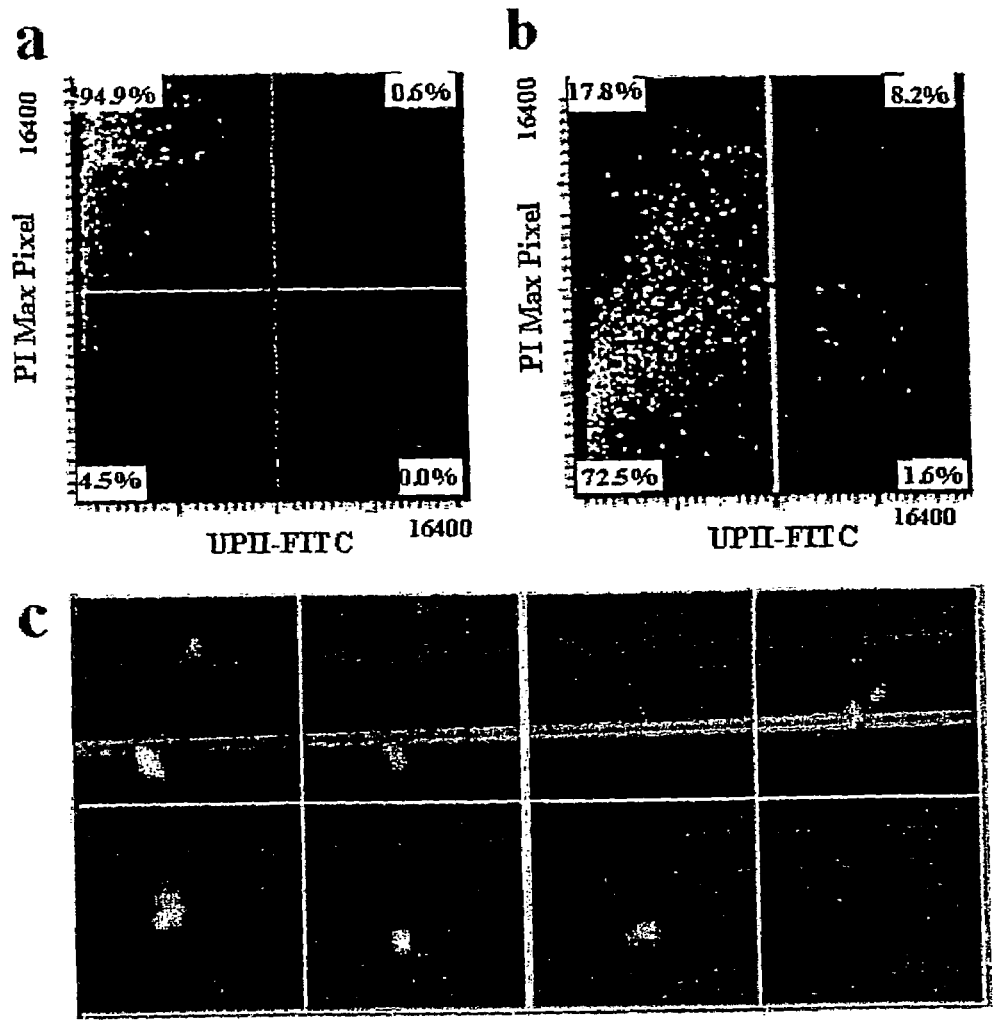
[FIG. 6]
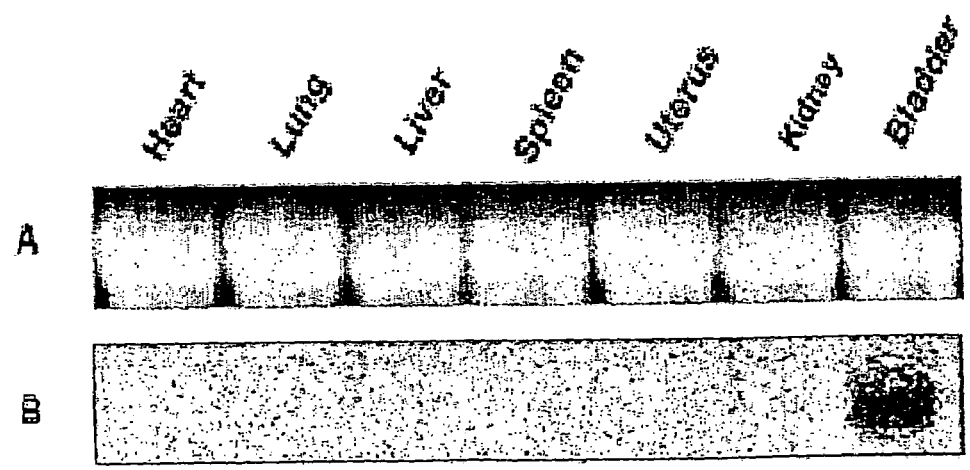

[FIG. 7]
a
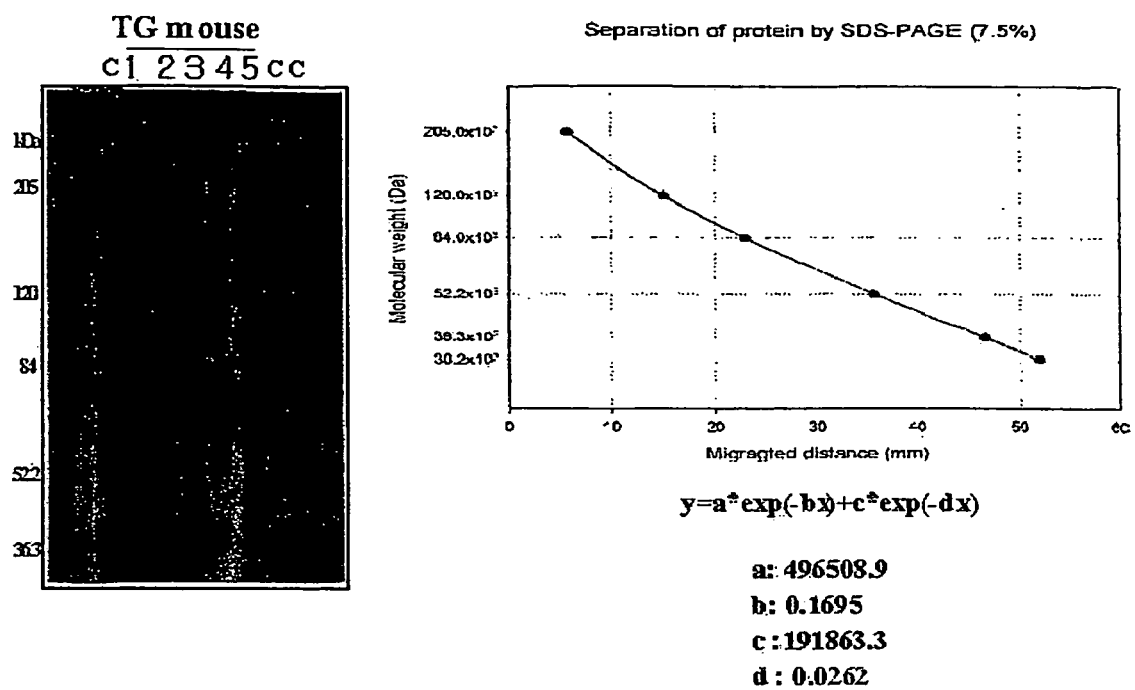
$y = a*\exp(-bx) + c*\exp(-dx)$
a: 496508.9
b: 0.1695
c: 191863.3
d: 0.0262
b
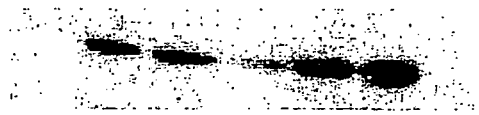

[FIG. 8]
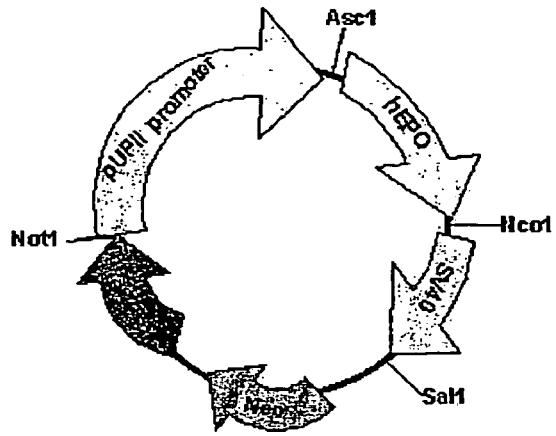
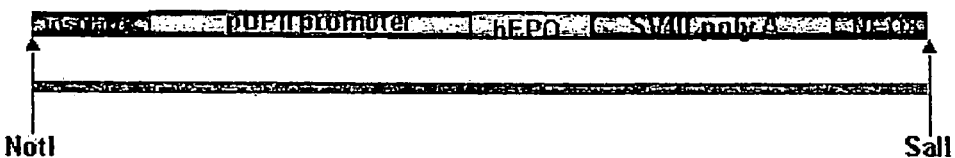
I/pUPII/hEPO (IUP2)
[FIG. 9]
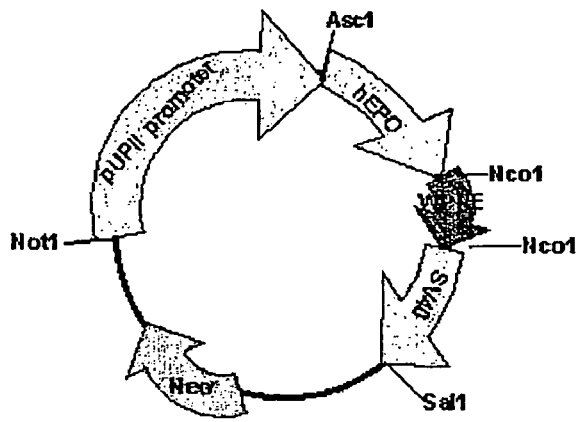
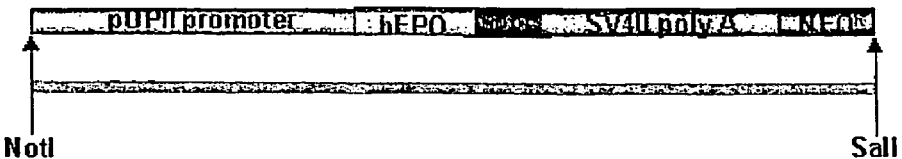
pUPII/hEPO/WPRE (PW)

[FIG. 10]
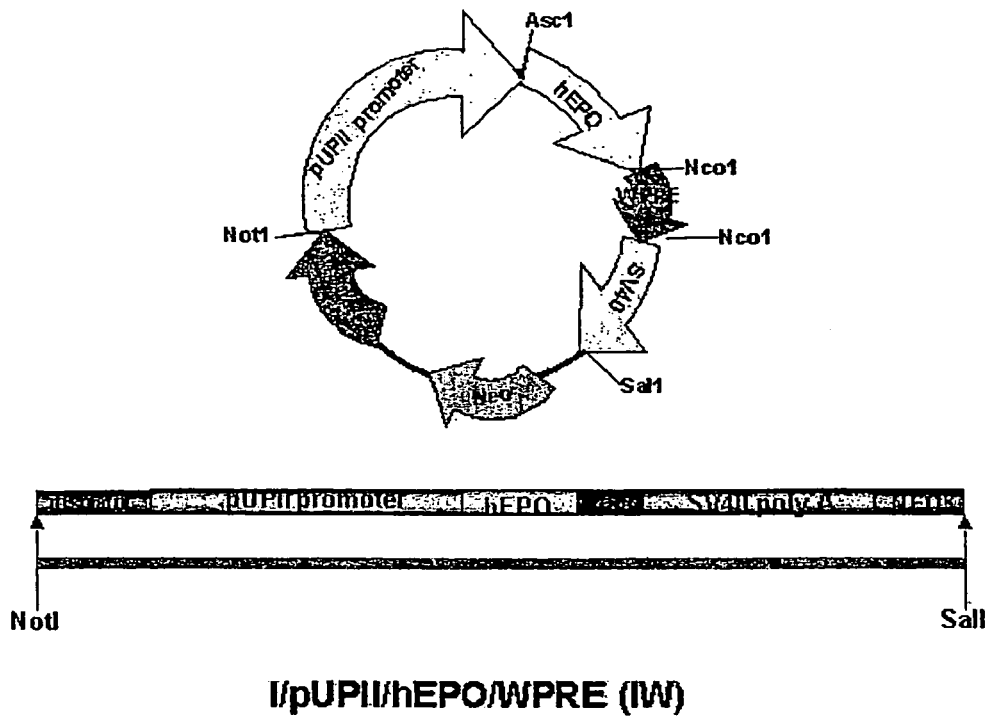
I/pUPII/hEPO/WPRE (IW)
[FIG. 11]
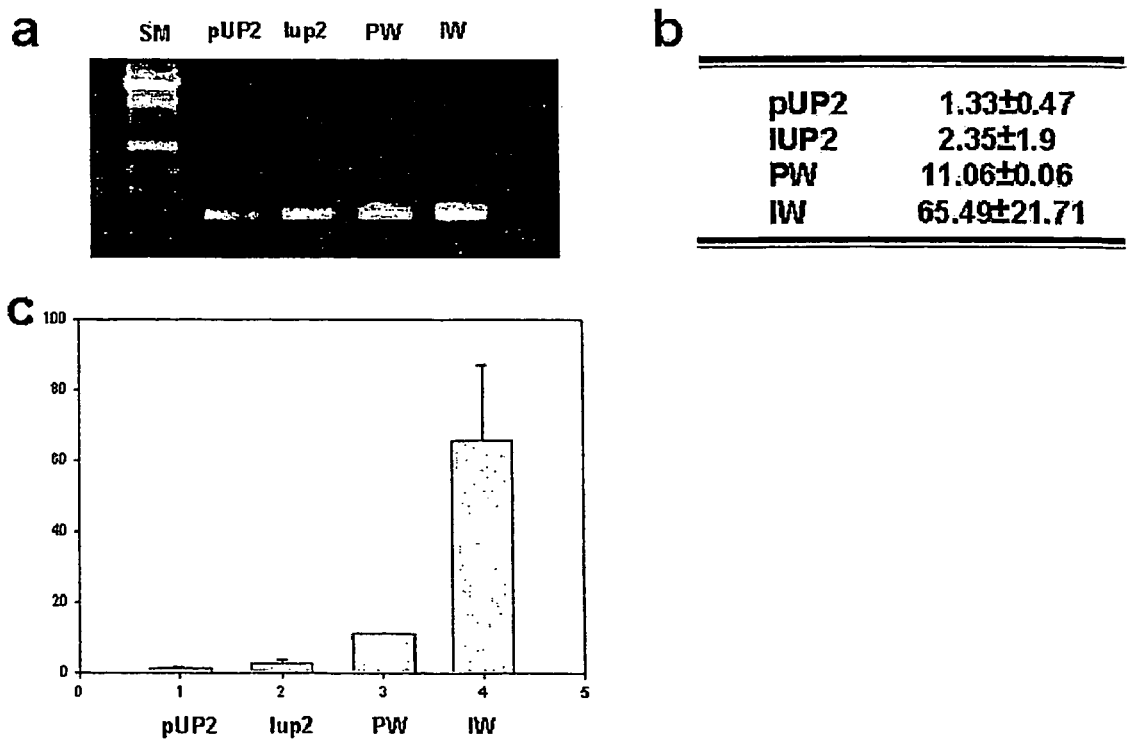
| | |
|---|---|
| pUP2 | 1.33±0.47 |
| IUP2 | 2.35±1.9 |
| PW | 11.06±0.06 |
| IW | 65.49±21.71 |

[FIG. 12]
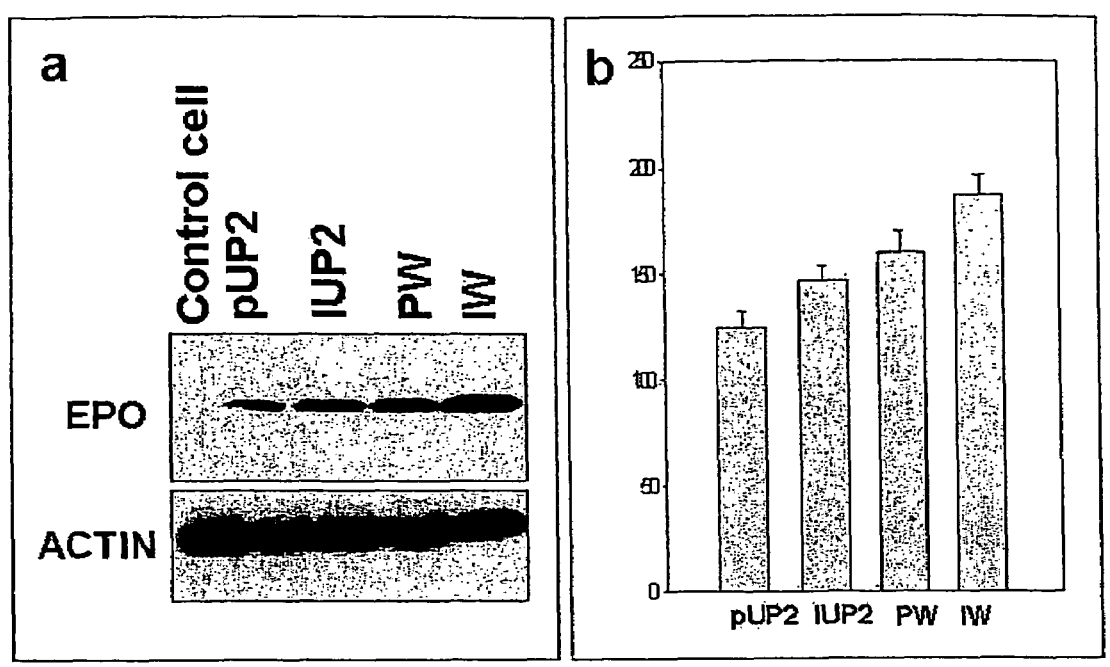

SEQUENCE LISTING

```
<160> NUMBER OF SEQ ID NOS: 13

<210> SEQ ID NO 1
<211> LENGTH: 8847
<212> TYPE: DNA
<213> ORGANISM: Sus scrofa
<220> FEATURE:
<221> NAME/KEY: promoter
<222> LOCATION: (1)..(8847)
<223> OTHER INFORMATION: porcine uroplakin II promoter
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (1261)..(1261)
<223> OTHER INFORMATION: n is a, c, g, or t
<220> FEATURE:
<221> NAME/KEY: misc_feature
<222> LOCATION: (1266)..(1266)
<223> OTHER INFORMATION: n is a, c, g, or t
<220> FEATURE:
<221> NAME/KEY: misc_feature
<222> LOCATION: (2446)..(2446)
<223> OTHER INFORMATION: n is a, c, g, or t
<220> FEATURE:
<221> NAME/KEY: misc_feature
```

```
<222> LOCATION: (3388)..(3388)
<223> OTHER INFORMATION: n is a, c, g, or t
<220> FEATURE:
<221> NAME/KEY: misc_feature
<222> LOCATION: (3790)..(3790)
<223> OTHER INFORMATION: n is a, c, g, or t
<220> FEATURE:
<221> NAME/KEY: misc_feature
<222> LOCATION: (3795)..(3795)
<223> OTHER INFORMATION: n is a, c, g, or t
<220> FEATURE:
<221> NAME/KEY: misc_feature
<222> LOCATION: (6882)..(6882)
<223> OTHER INFORMATION: n is a, c, g, or t
<220> FEATURE:
<221> NAME/KEY: misc_feature
<222> LOCATION: (6914)..(6914)
<223> OTHER INFORMATION: n is a, c, g, or t
<220> FEATURE:
<221> NAME/KEY: misc_feature
<222> LOCATION: (6916)..(6916)
<223> OTHER INFORMATION: n is a, c, g, or t

<400> SEQUENCE: 1
gggctaggag tggaatcaga gctggcctat gccacagcaa cgcagaatcc aaaccacatc    60
tccgacctac accagaccgt caccataaca caggatcctt aacccactga gcaaggtcag   120
ggatcaaacc caaatcctca tggatactag tcgggttctt aacccgctga gccacagtgg   180
gcactcctgt ttttgtttgt gtcttcgttt tttggctgca tctgcagcat acagaagttc   240
ctgggttaag gattgaaccc atgccacagc agcaacccga gccacagcag tgacaacagc   300
ctgatcctta actgctagac caccaggaa cgcccctca acttttcatg ccttggaaac   360
cctgagtcag tacaacctga caatngnttt ttttttttt ttttttgcc ttttctaggg   420 ccacttcccg cggcatgtgg agattcgcag gctanaggtc taatcggagc tgtagccacc   480
ggcctacacc agagccatag caacgaggga tccgagccga gtctgcaacc tacactacag   540
ctcatggcaa caccggatcg ttaacccact gagcaaggcc aggggatcga acccgcaacc   600
tcatggttcc tagtcagatt cgttaaccac tgcaccatga caggaactcc caacctgaca   660
attttatcat ttctgcaccc tagttgttga gtaatttgaa aaattcccaa gatgtcaagg   720
tcagtgtgat ggttaatttt atgtgtcaac ctgactaggc catgttgccc ggatgtggag   780
tcattgttat tctggatgtt actgtgaaga tatgttttgg atgaaattaa catttaaatc   840
agtgggggga aaaaagaag ttctcgttct ggtgcatcag aaacaaatcc gactaggaaa   900
caagcggttg caggttcgat ccctggcctc acttagtgga gtcaggatct ggcgttgccg   960
tgagctgtgg tacaggtggc agatgcagct cggatctagc attgctgtgg ctgtggtgta  1020
ggccagcagc tgtagctctg attaaacccc aagtctggga acctccatat gccgtgggtg  1080
tggcccgaaa aagcaaaaaa taaataaata aataaattta aaccagggga ttttgagcaa  1140
agcagattac cccataatat gggtgggtct catcaagttc attgtaggcc ctagtggaac  1200
aaagaccgac ctccaccttc tccccatgag aaggaaagaa ttctgccaaa agaccgcctt  1260
nggacntaaa ctgcaactct ttcctgagtt tccagcatgt tggcctcccc catcagactt  1320
tggacttgcc aagcctccgc aattgcatga gccaattcct taaaataaat ccgtctatat  1380
atacacatcc tgttggttct gtttctccag agaaccctga ctaacgcagt ctgcacccct  1440
gaagaccagt ggtccccaca ctcagctggg tgtcacctcc aaacactcag ccttcctcaa  1500
ggctctttct agctgtgtcc tcctctcccc acaacagctg tttcaaactc tcacccctct  1560
tcagggcgca atcccttctc ctccctgagt ttcctacttc ccagagaaag cagagacctt  1620
```

```
caggagtgtg ctgccttaac ttacttcctt catccctcag ccttgcaaaa gtataagctt    1680
tctctgcacc actgccccat tcttctctct gcagacaggg tcattcctaa agccaaacgc    1740
taatgcctcc acctctgatc tgagtcccat cttttccctc ctccagaagc ttcctcataa    1800
attctacccc cttttcttcc ttatctttat ctttgaaaac aaaatggaag acagccttcc    1860
cgttgtggtg cagcggaaac agtggtgcct tggaagcgct gggacgcagg ttcgacccct    1920
ggcccagcat agtaggttaa ggatccagtg ttgccacagt tttggcttag attgaaactg    1980
cagctcagat ctggtccctg cctgggaac ttcatacgcc acaggacggc ccaaaaagaa     2040
aagaaagaaa aaataaaaaa caaaacagaa agcctttcc tgtaccccca attccctcca     2100
gttatctctc tctttccctt cccagccaag ctctgcaaag agcggtctgc acagttctaa    2160
ctctacctcc tcccagttgg ccctggactt tctcagtctg gcttctaccc ccctcacccg    2220
taggaatctg ctctgaagga cacgcacccc tcacgatcct tggcccaggg acattttttg    2280
taccagcctt tcaatcctga ccttcatatc atccgacacc tcctttgtga aaccctccat    2340
ccactttctc ctggttcccc tcctaagacc cattccgcct tcttcagccc cctccctcca    2400
tctgtccttt agatgccgca tttcctagta tcctgtcctg cgcggnctcg tccttcccct   2460
ccacaactct cttcaaggac tctttttctcc atgtgcgatt ttgcccatgg cccaccttcc    2520
ctctctttac ccagactttc ccccggtgct ccagactcat agactcaatt atgaaaacat    2580
agttttcatc tgatttgccc aagatatttg cattagttat tactgtataa cagcttatcc    2640
cccaatttag tggcttataa ataaacact tattctgaga atcagaaacc taggcaggac     2700
atagttgggg tctcatgaag ttgcactgaa aatgtccccc tgggctaatc atacggagga    2760
ctgaccaggg ctggaggatc tgttccaagc tcattcattc acatggccgt aggttggaga    2820
cagctcttct ctggatcttg gcaggagcct caattccttg tcacgtggac ctccccttgg    2880
agggggtccc atgtcctcca tggtgagtaa tccatgagag caaggtggaa ggtgccatgc    2940
catttaggac ctagcctcag gagggaccta cgtcacttct gttgtagtct gttggccaca    3000
cagactaacc ctgacacaat gcacccatcc atgacctgct gccagtccat tctccacact    3060
gtttccagaa tgatatttac ataagtaaaa ctcctcaaag gcttttgaga ttttttttcc    3120
cattatagtt gatttataac ctcagaggct tttgttttct tcagcataaa aaccaagttc    3180
cttaacatag catgtaaccc actggccacc ctgccagtgg ctagaactct caccatgtcc    3240
atccttgaat actgctttct agccaagagc tattgtttgc agttcccaga atgtgtcggg    3300
ataactcaca tctctgagcc ttttcatgtg ctgttccctc actttggaat atcccccttcc   3360 atttaggaag gctaatgtcc attcattntc caaaactcag aagcaaattt tttttttttt    3420
tttttttttt tttttttgct tttagggcc gaactctcag catatggagg ttcccaggtt     3480
agccatcaaa ttggaattgt agctgctggc ctacaccaca gccatagcaa caccagaccc    3540
aagtcacatc tgcaacctac atcacagatc atggcaatac tggatcctta acccactgag    3600
tgagcccagg gatcaaacac aaattctcat ggatactcgc caggttcatt accactgagc    3660
cacaacagga actcctctcc tttttatggt cacacctgca gcatatggaa gttcctgggc    3720
cagggattga atctgagtgg cagctgtgac aatgccgtat cctttaattc actgtgctgg    3780
gctgaggggn taaantgccc ctcctaaaaa acctgagctg ctgcagttgg attcttaatc    3840
cactgcacca aaggggggaa ggtcaagaac tgtcttgcca tctctgtatc ttatcaccta    3900
gcatagtacc caccatagag aagttgctca acaaatgttt actgaatgaa taatgcatg     3960 agctggagtt cccattgcgg ctcagcagta acaaacctga ctagcattca taagaacttg    4020
```

-continued

```
ggttcgatcc ctagcctcag tgggttaagg atgcagcatt gctgtgagct gtggtgtagg      4080
tcgcagacga cactcagatc ccacattgct gtcactgtgg cgcaggccgg cctctgtagc      4140
tctgattcga ctcctagcct gggaacgtcc atatgccaca ggtgaggccc taaaagaaa       4200 taaataagca agcaagtaag caagcaggca gtttcttggt gccttgtacc cctgtggcct      4260
gtgtggtata caagtaacag ctgatccatg tctcagtcat gtttcccct cagactacct      4320 ttcctgcccc atctctccct ttgacataat tggaaaaaca aattcagaat tttgtcccac      4380
tacctttctt gctagctctg tggccttggg aaagctattt attgcctctg agcctctaat      4440
tttcatctgc accaaggatt aataaaaagg agaggataag atgaattact tatattaata      4500
tttattgaac cagatactgt gctaggcact cttaaataaa ttagcttgag tgatagtcat      4560
agtatcctgg tgagacagat ttttttttc cttttatggt tgcacgtgca acatatggaa       4620
gttcctgggc tggggtcgaa ttggagctgc aggtgcttgc ctatgccaca gccatggcaa      4680
catcatatac aaaccgcacc tgtgacctac accacagatt gcagcaacgc tggatccttc      4740
acccaaggag caaggccagg aatcaaatgt gcatcctcac aaacactatg tccggttttt      4800
aacccgctga gccacaccag gaactccatg gcgagacaga ttttatactc tgtctacaga      4860
agaggaaagt gaagctcaga atggttaggt aggtaacttg gccaagatca aaaaattcaa      4920
agaagatttg gggcaagtgg tgatatcatg gcagcattag aaaaaataaa gaagcatcca      4980
cttgttttcc aacactgaac aactgagatt ttcttactct cacagctttt tccagcttca      5040
tatccaagga cagacgctct gccatttcc catcagacca atatttgctg aacactgcac      5100 cttacttt aggtccaagt caccaggggt tttcccagtt tgctcctaca gattctgaca       5160
ctatctccac attttttttg cacctttatt ttaaagcatt tttatacctg tcatacctg      5220 ctagataaat gggaaggaat gaatcttccc atttataggt gagaaaattg aggttcaaag      5280
tgactcacca aaagtcatat agcatcactc ctcaacagga ggacagcagt ccccaccaga      5340
gggtaacatg tccatggagc ctagtggaca cattttcta actgactggg aagcagcaga      5400
gtggtattgt gaaggggggaa tcataggtat atcaaacaga cttaggttct gatccgagct      5460
attctgcttg caaacaacca tagttcaatt taaaaaaaaa aagaaagaa agaaagaaag      5520 aaaggagccc ccatcctggt gcagtggaaa caaattcaac taggaactgt gaggttgtgg      5580
gttcgatccc tggccttgct cagtgggtta aggatctggc gttgccatga gccgtggtgt      5640
aggttgcaga ctcaactcag atctggcgtt gctgtgactg tggctgtgat gtaggctggc      5700
agctgtaact ccggttagac cccagcctgg gaacctccat atgcaacctc catatgcggt      5760
gggtgtggcc ctaaaagaa aaaaaaaaa aaagaggaa ttcccttatg gctcagcagg      5820
ttaaggatct ggtattgtca ctgctgtggc tctagttaca gccatagtgc aggttcaatc      5880
cctggcccag gaacgtctgc atcccacagg tgtggccaaa aagaaagaa aggaaggagt      5940 tctgttgtgg cacaatagga ttggcaacat cttaggagta ctgggacaca ggttcaatcc      6000
ctggcccagc acagtgggta aggagccagt gttgctggtc aaaaaagaaa agaaaaagta      6060
ccatagttag agtaaatctg ttttaggagc tattctttgg ggcagaacag agagatcagg      6120
agctccttga gagcagaaac ttacctttac atccctcgtg cctagcacgg ttctaggggc      6180
atacctggta tttaataaat atagccaact ggatagggga ttggaaggaa agagcagggg      6240
agggaacttg agtgagttga aaattgaga atccaaaggg gagacagcct agaaagagta      6300
ggtccaagaa agagatccca ggcatttgtg gccctggttc ccttttttcca agccatgagg      6360
```

```
aaatcctcag aggaacagag tgctgtggct ttaaatgact tcagcgttgt caatgaatct    6420
gctcggctaa aagagttatc ctcttgctcc ttcgcttgtc ctcccctcc tctcagctcc     6480 ccaaacccct tctcggctgct gtgatgggat aattagatgc gagagctcag cacagatgat   6540
gctccagttg cctagcaact aatggtttcc atggagaccg caaagcacag cctccagagc    6600
agccagtgag cagctcggca gggcagggag aagacgcaac tctcagctcc tccagaaacc    6660
tggggagggc caggagtggg gaagaagggg gggatcggag ggcttaaagg cacaggcccc    6720
tcttatcctc ttaaaatctg gtcagagctc tgccctcccc tcccctactc tgtcccactc    6780
ataatttcag atggagttgg gggcttagga gtggacccaa cacaacctac cctgcaataa    6840
acccaacctt ctttctgctt ctggtttgtg gctgaaaatg gnaaaagaaa tctcccaagt    6900
gcaagtgtaa acancntcct gggttggcaa tgggatctga agagtactaa gatccctcag    6960
acctggaatt ccaccattta gtctttccct ctctccaaag ttctcaatgt gcaaaagatc    7020
ctctttcagt ttgcagagca atgataggat cttctaaaag gagacaaaag ccaaggtgca    7080
ggaaaaatag aattcagttc ttcacccaaa ggcagcctgt cctgggagac aggggtgaaa    7140
cacttggtcc tgatctccat cagaggatcc agagtgtgtg tgtttgttgc tggggagggg    7200
gacacaatat agagcatctg gtgactcaaa gtatgtgcct cccagagtag catcaatcaa    7260
tgttacctgg aagcttgtta gaaatgcaga atttcaggct tcacctcaga cccactgaat    7320
cagaaactgc atcttaacaa gatccctcat gattcatacg cacattaaat ttggagaagc    7380
gctgacctga gaccctcctc ctctctgctt gggcccatag ttctaccttt attgtcacct    7440
cgtctcacct cgtgctcata ccccaggctt tgagcctacc cttcccccca tggggaaagg    7500
acacaaggcc accagcccct cacttcccta ccaggaccct ggccctcctc tgggactgga    7560
gaaggacaaa gaggaccccc tctgtggagg tctacgacct ctcctgacca agtagtccac    7620
tcaccacaag tggctctacc tctctgagtc tcagtttcca catccacaaa aggtggccaa    7680
tgctatctgc cacccagaat ggctgtgagg gtggagcagg caaagcctct gtgccatcag    7740
agaaattgtg tctcttttc attttctccc agtgggtttc tttctcgtct ttattctttt     7800
tttttttttt ttttcctgtc tgttgtattt ttagggccgt gcctgtggca tacggaagtt    7860
cccagggtag gggtccaatg ggagctgtag ccccgggcct acgccacagc cacagcaatg    7920
tgggatctga gccacgtctg caacctacac cacagctcac ggcaacacca gatccttaac    7980
ccactgagca aggccaggga tcgagcccac gtcctcatgg atgctagttg ggttcgttaa    8040
ccgctgagcc atgatgataa ctcctctttc tattctttag tcacaaacag tcaacaaagg    8100
ttgctgacca aggctgatcg tgcccacccc ccagccccc agactgggcc agtgccacc     8160 ccttgggtct ctctggaaat cctgcccagc atcaattggc tccactctcc aggaggatgg    8220
gaagccctgt ggcccctggg actcacaccc ctctgcatct cccagagtgc aggacctggt    8280
cttcaggaga caccaagaac tggctccccc ggctctgctg ccccaccccc ctactaccag    8340
tttctctccc attcctgccc agtccaggcc ccctggggtt actctcctct ctctgtacac    8400
cagtgcaacc tcagaacctg cttccctcct gggaacaccc actaccacgt gggagaaggg    8460
gtcgtctagg ggttgggccc cagatacact tgtaagcagg aacacacgag cccttacatg    8520
tgggtgtccc ggaagaaggg ggttttccac ccccgctttt agtcaccctg ccctctgca     8580 gctgcctgag ccaccaagac ccagccaagg tctcctgcct tctggcctga ggccagctc    8640 cccatcctga aaaacctgtc tgggggcctc cctgaggct gtaggcccca aggcctcccc    8700
tgaggctgta gggcccaagg ggcaggttga acaggattcc cctctggccc ctcctacccc    8760
```

```
caggacaaaa ccagagcccc aggacagggc ctcacttgcc tcaggaaacc acagcttgcc    8820
agcacccagc ccagcaccag cccagct                                        8847

<210> SEQ ID NO 2
<211> LENGTH: 20
<212> TYPE: DNA
<213> ORGANISM: Artificial sequence
<220> FEATURE:
<223> OTHER INFORMATION: forward primer for amplifying porcin uroplakin
      II gene

<400> SEQUENCE: 2
gatcctgatt ctgctggctb                                                  20

<210> SEQ ID NO 3
<211> LENGTH: 20
<212> TYPE: DNA
<213> ORGANISM: Artificial sequence
<220> FEATURE:
<223> OTHER INFORMATION: reverse primer for amplifying porcin uroplakin
      II gene

<400> SEQUENCE: 3
atggtggtca tcacrgtgct                                                  20

<210> SEQ ID NO 4
<211> LENGTH: 3602
<212> TYPE: DNA
<213> ORGANISM: Homo sapiens
<300> PUBLICATION INFORMATION:
<301> AUTHORS: Lin, F. K., Suggs, S., Lin, C. H., Browne, J. K.,
      Smalling, R., Egrie, J. C., Chen, K. K., Fox, G. M., Martin, F.,
      Stabinsky, Z.
<302> TITLE: Cloning and expression of the human erythropoietin gene
<303> JOURNAL: Proc. Natl. Acad. Sci. U.S.A.
<304> VOLUME: 82
<306> PAGES: 7580-7584
<307> DATE: 1985

<400> SEQUENCE: 4
aagcttctgg gcttccagac ccagctactt tgcggaactc agcaacccag gcatctctga     60
gtctccgccc aagaccggga tgcccccag gggaggtgtc cgggagccca gcctttccca    120
gatagcacgc tccgccagtc ccaagggtgc gcaaccggct gcactcccct cccgcgaccc    180
agggcccggg agcagccccc atgacccaca cgcacgtctg cagcagcccc gctcacgccc    240
cggcgagcct caacccaggc gtcctgcccc tgctctgacc ccgggtggcc cctacccctg    300 gcgaccctc acgcacacag cctctccccc acccccaccc gcgcacgcac acatgcagat    360
aacagccccg accccggcc agagccgcag agtccctggg ccaccccggc cgctcgctgc    420
gctgcgccgc accgcgctgt cctcccggag ccggaccggg ccaccgcgc ccgctctgct    480 ccgacaccgc gccccctgga cagccgccct ctcctctagg cccgtggggc tggccctgca    540
ccgccgagct tcccgggatg agggcccccg gtgtggtcac ccggcgcgcc ccaggtcgct    600
gagggacccc ggccaggcgc ggagatgggg gtgcacggtg agtactcgcg gctgggcgc    660 tcccgccgcc cgggtccctg tttgagcggg gatttagcgc cccggctatt ggccaggagg    720 tggctggggtt caaggaccgg cgacttgtca aggaccccgg aaggggagg ggggtggggc    780 agcctccacg tgccagcggg gacttggggg agtccttggg gatggcaaaa acctgacctg    840 tgaagggggac acagtttggg ggttgagggg aagaaggttt gggggttctg ctgtgccagt    900
ggagaggaag ctgataagct gataacctgg gcgctggagc caccacttat ctgccagagg    960
```

```
ggaagcctct gtcacaccag gattgaagtt tggccggaga agtggatgct ggtagctggg    1020
ggtggggtgt gcacacggca gcaggattga atgaaggcca gggaggcagc acctgagtgc    1080
ttgcatggtt ggggacagga aggacgagct ggggcagaga cgtggggatg aaggaagctg    1140
tccttccaca gccacccttc tccctccccg cctgactctc agcctggcta tctgttctag    1200
aatgtcctgc ctggctgtgg cttctcctgt ccctgctgtc gctccctctg ggcctcccag    1260
tcctgggcgc cccaccacgc ctcatctgtg acagccgagt cctggagagg tacctcttgg    1320
aggccaagga ggccgagaat atcacggtga accccttcc ccagcacatt ccacagaact     1380
cacgctcagg gcttcaggga actcctccca gatccaggaa cctggcactt ggtttggggt    1440
ggagttggga agctagacac tgccccccta cataagaata agtctggtgg ccccaaacca    1500
tacctggaaa ctaggcaagg agcaaagcca gcagatccta cggcctgtgg gccagggcca    1560
gagccttcag ggacccttga ctccccgggc tgtgtgcatt tcagacgggc tgtgctgaac    1620
actgcagctt gaatgagaat atcactgtcc cagacaccaa agttaatttc tatgcctgga    1680
agaggatgga ggtgagttcc tttttttttt tttttccttt cttttggaga atctcatttg    1740
cgagcctgat tttggatgaa agggagaatg atcggggaa aggtaaaatg gagcagcaga     1800
gatgaggctg cctgggcgca gaggctcacg tctataatcc caggctgaga tggccgagat    1860
gggagaattg cttgagccct ggagtttcag accaacctag gcagcatagt gagatccccc    1920
atctctacaa acatttaaaa aaattagtca ggtgaagtgg tgcatggtgg tagtcccaga    1980
tatttggaag gctgaggcgg gaggatcgct tgagcccagg aatttgaggc tgcagtgagc    2040
tgtgatcaca ccactgcact ccagcctcag tgacagagtg aggccctgtc tcaaaaaaga    2100
aaagaaaaaa gaaaaataat gagggctgta tggaatacat tcattattca ttcactcact    2160
cactcactca ttcattcatt cattcattca acaagtctta ttgcatacct tctgtttgct    2220
cagcttggtg cttggggctg ctgaggggca ggagggagag ggtgacatgg gtcagctgac    2280
tcccagagtc cactccctgt aggtcgggca gcaggccgta gaagtctggc agggcctggc    2340
cctgctgtcg gaagctgtcc tgcggggcca ggccctgttg gtcaactctt cccagccgtg    2400
ggagcccctg cagctgcatg tggataaagc cgtcagtggc cttcgcagcc tcaccactct    2460
gcttcgggct ctgggagccc aggtgagtag gagcggacac ttctgcttgc cctttctgta    2520
agaaggggag aagggtcttg ctaaggagta caggaactgt ccgtattcct tcccttctg    2580 tggcactgca gcgacctcct gttttctcct tggcagaagg aagccatctc ccctccagat    2640
gcggcctcag ctgctccact ccgaacaatc actgctgaca cttccgcaa actcttccga    2700 gtctactcca atttcctccg gggaaagctg aagctgtaca caggggaggc ctgcaggaca    2760
ggggacagat gaccaggtgt gtccacctgg gcatatccac cacctccctc accaacattg    2820
cttgtgccac accctccccc gccactcctg aaccccgtcg aggggctctc agctcagcgc    2880
cagcctgtcc catggacact ccagtgccag caatgacatc tcaggggcca gaggaactgt    2940
ccagagagca actctgagat ctaaggatgt cacagggcca acttgagggc ccagagcagg    3000
aagcattcag agagcagctt taaactcagg acagagcca tgctgggaag acgcctgagc     3060
tcactcggca ccctgcaaaa tttgatgcca ggacacgctt tggaggcgat ttacctgttt    3120
tcgcacctac catcagggac aggatgacct ggagaactta ggtggcaagc tgtgacttct    3180
ccaggtctca cgggcatggg cactcccttg gtggcaagag cccccttgac accggggtgg    3240
tgggaaccat gaagacagga tgggggctgg cctctggctc tcatggggtc caagttttgt    3300
```

-continued

```
gtattcttca acctcattga caagaactga aaccaccaat atgactcttg gcttttctgt    3360
tttctgggaa cctccaaatc ccctggctct gtcccactcc tggcagcagt gcagcaggtc    3420
caggtccggg aaatgagggg tggaggggc tgggccctac gtgctgtctc acacagcctg    3480
tctgacctct cgacctaccg gcctaggcca caagctctgc ctacgctggt caataaggtg    3540
tctccattca aggcctcacc gcagtaaggc agctgccaac cctgcccagg gcaaggctgc    3600
ag                                                                   3602
```

<210> SEQ ID NO 5
<211> LENGTH: 1916
<212> TYPE: DNA
<213> ORGANISM: Gallus gallus
<220> FEATURE:
<221> NAME/KEY: misc_feature
<222> LOCATION: (1)..(1916)
<223> OTHER INFORMATION: beta-globin insulator

<400> SEQUENCE: 5

```
gcggccgcgc gcgtcaggtg gcacttttcg gggaaatgtg cgcggaaccc ctatttgttt      60 attttttctaa atacattcaa atatgtatcc gctcatgaga caataaccct gataaatgct    120
tcaataatat tgaaaaagga agagtcctga ggcggaaaga accagctgtg aatgtgtgt     180 cagttagggt gtggaaagtc cccaggctcc ccagcaggca gaagtatgca aagcatgcat    240
ctcaattagt cagcaaccag gtgtggaaag tccccaggct cccagcagg cagaagtatg     300 caaagcatgc atctcaatta gtcagcaacc atagtcccgc ccctaactcc gcccatcccg    360
cccctaactc cgcccagttc cgcccattct ccgccccatg gctgactaat ttttttatt     420 tatgcagagg ccgaggccgc ctcggcctct gagctattcc agaagtagtg aggaggcttt    480
tttggaggcc taggcttttg caaagatcga tcaagagaca ggatgaggat cgtttcgcat    540
gattgaacaa gatggattgc acgcaggttc tccggccgct tgggtggaga ggctattcgg    600
ctatgactgg gcacaacaga caatcggctg ctctgatgcc gccgtgttcc ggctgtcagc    660
gcaggggcgc ccggttcttt ttgtcaagac cgacctgtcc ggtgccctga atgaactgca    720
agacgaggca gcgcggctat cgtggctggc cacgacgggc gttccttgcg cagctgtgct    780
cgacgttgtc actgaagcgg gaagggactg gctgctattg ggcgaagtgc cggggcagga    840
tctcctgtca tctcaccttg ctcctgccga gaaagtatcc atcatggctg atgcaatgcg    900
gcggctgcat acgcttgatc cggctacctg cccattcgac caccaagcga acatcgcat    960 cgagcgagca cgtactcgga tggaagccgg tcttgtcgat caggatgatc tggacgaaga   1020
gcatcagggg ctcgcgccag ccgaactgtt cgccaggctc aaggcgagca tgcccgacgg   1080
cgaggatctc gtcgtgaccc atggcgatgc ctgcttgccg aatatcatgg tggaaaatgg   1140
ccgcttttct ggattcatcg actgtggccg gctgggtgtg gcggaccgct atcaggacat   1200
agcgttggct acccgtgata ttgctgaaga gcttggcggc gaatgggctg accgcttcct   1260
cgtgctttac ggtatcgccg ctcccgattc gcagcgcatc gccttctatc gccttcttga   1320
cgagttcttc tgagcgggac tctggggttc gaaatgaccg accaagcgac gcccaacctg   1380
ccatcacgag atttcgattc caccgccgcc ttctatgaaa ggttgggctt cggaatcgtt   1440
ttccgggacg ccggctggat gatcctccag cgcggggatc tcatgctgga gttcttcgcc   1500
caccctaggg ggaggctaac tgaaacacgg aaggagacaa taccggaagg aacccgcgct   1560
atgacggcaa taaaaagaca gaataaaacg cacggtgttg ggtcgtttgt tcataaacgc   1620
ggggttcggt cccagggctg gcactctgtc gatacccac cgagacccca ttggggccaa    1680
```

```
tacgcccgcg tttcttcctt ttccccaccc cacccccccaa gttcgggtga aggcccaggg    1740
ctcgcagcca acgtcggggc ggcaggcccc gccatagcct caggttactc atatatactt    1800
tagattgatt taaaacttca ttttttaattt aaaaggatct aggtgaagat ccttttttgat    1860 aatctcatga ccaaaatccc ttaacgtgag ttttcgttcc actgagcgtc cgatcg         1916
```

<210> SEQ ID NO 6
<211> LENGTH: 2254
<212> TYPE: DNA
<213> ORGANISM: Artificial sequence
<220> FEATURE:
<223> OTHER INFORMATION: cloning vector pEGFP-N1, complete sequence,
      enhanced green fluorescent protein (egfp) and neomycin
      phosphotransferase genes

<400> SEQUENCE: 6

```
tcgactctag agggacagcc ccccccccaaa gccccccaggg atgtaattac gtccctcccc    60
cgctaggggc agcagcgagc cgcccggggc tccgctccgg tccggcgctc cccccgcatc    120
cccgagccgg cagcgtgcgg ggacagcccg ggcacgggga aggtggcacg ggatcgcttt    180
cctctgaacg cttctcgctg ctctttgagc ctgcagacac ctgggggggat acggggaaaa    240 agctttaggc tgaaagagag atttagaatg acagaatcat agaacggcct gggttgcaaa    300
ggagcacagt gctcatccag atccaacccc ctgctatgtg cagggtcatc aaccagcagc    360
ccaggctgcc cagagccaca tccagcctgg ccttgaatgc ctgcagggat ggggcatcca    420
cagcctcctt gggcaacctg ttcagtgcgt caccaccctc tggggaaaaa actgcctcct    480
catatccaac ccaaacctcc cctgtctcag tgtaaagcca ttcccccttg tcctatcaag    540 gggggagttttg ctgtgacatt gttggtctgg ggtgacacat gtttgccaat tcagtgcatc    600
acggagaggc agatcttggg gataaggaag tgcaggacag catggacgtg ggacatgcag    660
gtgttgaggg ctctgggaca ctctccaagt cacagcgttc agaacagcct taaggataag    720
aagataggat agaaggacaa agagcaagtt aaaacccagc atggagagga gcacaaaaag    780
gccacagaca ctgctggtcc ctgtgtctga gcctgcatgt ttgatggtgt ctggatgcaa    840
gcagaagggg tggaagagct tgcctggaga gatacagctg ggtcagtagg actgggacag    900
gcagctggaa aattgccatg tagatgttca tacaatcgtc aaatcatgaa ggctggaaag    960
cctccaagat ccccaagacc aaccccaacc cacccaccgt gcccactggc catgtccctc    1020
agtgccacat ccccacagtt cttcatcacc tccaggacg tgaccccccc cacctccgtg    1080
ggcagctgtg ccactgcagc accgctcttt ggagaaggta atcttgcta atccagccc    1140 gaccctcccc tggcacaacg taaggccatt atctctcatc caactccagg acggagtcag    1200
tgaggatggg gctctagagg gacagccccc ccccaaagcc cccagggatg taattacgtc    1260
cctcccccgc taggggcagc agcgagccgc ccggggctcc gctccggtcc ggcgctcccc    1320
ccgcatcccc gagccggcag cgtgcgggga cagcccgggc acggggaagg tggcacggga    1380
tcgctttcct ctgaacgctt ctcgctgctc tttgagcctg cagacacctg ggggggatacg    1440 gggaaaaagc tttaggctga aagagagatt tagaatgaca gaatcataga acggcctggg    1500
ttgcaaagga gcacagtgct catccagatc caaccccctg ctatgtgcag ggtcatcaac    1560
cagcagccca ggctgcccag agccacatcc agcctggcct tgaatgcctg cagggatggg    1620
gcatccacag cctccttggg caacctgttc agtgcgtcac caccctctgg ggaaaaaact    1680
gcctcctcat atccaaccca aacctcccct gtctcagtgt aaagccattc cccccttgtcc    1740
```

```
tatcaagggg gagtttgctg tgacattgtt ggtctggggt gacacatgtt tgccaattca    1800
gtgcatcacg gagaggcaga tcttggggat aaggaagtgc aggacagcat ggacgtggga    1860
catgcaggtg ttgagggctc tgggacactc tccaagtcac agcgttcaga acagccttaa    1920
ggataagaag ataggataga aggacaaaga gcaagttaaa acccagcatg gagaggagca    1980
caaaaaggcc acagacactg ctggtccctg tgtctgagcc tgcatgtttg atggtgtctg    2040
gatgcaagca aagggggtcc atgtccctca gtgccacatc cccacagttc ttcatcacct    2100
ccagggacgg tgacccccc acctccgtgg gcagctgtgc cactgcagca ccgctctttg     2160
gagaaggtaa atcttgctaa atccagcccg accctcccct ggcacaacgt aaggccatta    2220
tctctcatcc aactccagga acggagtcag tgag                                 2254
```

<210> SEQ ID NO 7
<211> LENGTH: 632
<212> TYPE: DNA
<213> ORGANISM: Woodchuck hepatitis B virus
<220> FEATURE:
<221> NAME/KEY: misc_feature
<222> LOCATION: (1)..(632)
<223> OTHER INFORMATION: woodchuck hepatitis virus posttranscriptional
      regulatory element

<400> SEQUENCE: 7

```
accaggttct gttcctgtta atcaacctct ggattacaaa atttgtgaaa gattgactgg     60
tattcttaac tatgttgctc cttttacgct atgtggatac gctgctttaa tgcctttgta    120
tcatgctatt gcttcccgta tggctttcat tttctcctcc ttgtataaat cctggttgct    180
gtctctttat gaggagttgt ggcccgttgt caggcaacgt ggcgtggtgt gcactgtgtt    240
tgctgacgca accccactg gttggggcat tgccaccacc tgtcagctcc tttccgggac     300
tttcgctttc cccctcccta ttgccacggc ggaactcatc gccgcctgcc ttgcccgctg    360
ctggacaggg gctcggctgt tgggcactga caattccgtg gtgttgtcgg ggaagctgac    420
gtcctttcca tggctgctcg cctgtgttgc cacctggatt ctgcgcggga cgtccttctg    480
ctacgtccct tcggccctca atccagcgga ccttccttcc gcggcctgc tgccggctct     540 gcggcctctt ccgcgtcttc gccttcgccc tcagacgagt cggatctccc tttgggccgc    600
ctccccgcct gtttcgcctc gggctcctcg ag                                   632
```

<210> SEQ ID NO 8
<211> LENGTH: 24
<212> TYPE: DNA
<213> ORGANISM: Artificial sequence
<220> FEATURE:
<223> OTHER INFORMATION: forward primer for amplifying neomycin
      resistant gene

<400> SEQUENCE: 8

```
gcggccgcgc gcgtcaggtg gcac                                             24
```

<210> SEQ ID NO 9
<211> LENGTH: 29
<212> TYPE: DNA
<213> ORGANISM: Artificial sequence
<220> FEATURE:
<223> OTHER INFORMATION: reverse primer for amplifying neomycin
      resistant gene

<400> SEQUENCE: 9

```
cgatcggacg ctcagtggaa cgaaaactc                                        29
```

```
<210> SEQ ID NO 10
<211> LENGTH: 18
<212> TYPE: DNA
<213> ORGANISM: Artificial sequence
<220> FEATURE:
<223> OTHER INFORMATION: forward primer for amplifying chicken B-globin
      insulator

<400> SEQUENCE: 10
tcgactctag agggacag                                                     18

<210> SEQ ID NO 11
<211> LENGTH: 18
<212> TYPE: DNA
<213> ORGANISM: Artificial sequence
<220> FEATURE:
<223> OTHER INFORMATION: reverse primer for amplifying chicken B-globin
      insulator

<400> SEQUENCE: 11
ctcactgact ccgttcct                                                     18

<210> SEQ ID NO 12
<211> LENGTH: 29
<212> TYPE: DNA
<213> ORGANISM: Artificial sequence
<220> FEATURE:
<223> OTHER INFORMATION: forward primer for amplifying woodchuck
      hepatitis virus posttranscriptional regulatory element

<400> SEQUENCE: 12
accaggttct gttcctgtta atcaacctc                                         29

<210> SEQ ID NO 13
<211> LENGTH: 27
<212> TYPE: DNA
<213> ORGANISM: Artificial sequence
<220> FEATURE:
<223> OTHER INFORMATION: reverse primer for amplifying woodchuck
      hepatitis virus posttranscriptional regulatory element

<400> SEQUENCE: 13
ctcgaggagc ccgaggcgaa acaggcg                                           27
```

PORCINE UROPLAKIN II PROMOTER AND THE PRODUCTION METHOD OF USEFUL PROTEINS USING SAID PROMOTER

TECHNICAL FIELD

The present invention relates to a porcine uroplakin II gene promoter and a method for producing useful proteins using the same.

BACKGROUND ART

In the medicinal field, as a method for maximizing the production of proteins such as EPO with high economic-value-added, a mass production method using cell culture technology has been mainly used However, in this method, production cost is increased due to the use of animal blood as a culture medium, and expert knowledge is required for culture. Furthermore, since it is impossible to completely isolate a freshly produced EPO from an animal EPO contained in the culture medium, there is a problem in that a finally produced EPO has low purity and activity.

On the other hand, in a method for producing useful proteins using transgenic animals, a target protein is contained in body fluids secreted by the animals, so that a target protein is easily isolated and purified and maintains superior activity as compared to the existing cell-culture technology. For this reason, an interest in this method is being rapidly increased.

In the transgenic animal technology developed till now, mammary gland known to show high protein expression was mainly used as an organ for producing a target protein. However, the results of animal tests showed that it is ultimately impossible to produce several important target proteins, such as EPO, by expression in milk, due to expression in other tissues as well as the mammary gland. Furthermore, since various proteins such as albumin are originally contained in milk at large amounts, the resulting target proteins are difficult to purify.

In an attempt to overcome such problems, a method for producing useful proteins using the bladder is recently proposed.

The bladder produces urine throughout animal's life regardless of the age and sex of animals, and the urine contains protein and fatty components at only a very small amount of 5-25 mg/l. Thus, the use of the bladder makes the isolation and purification of target proteins significantly easy.

However, the protein production efficiency of animals transformed with bladder-specific promoters developed up to now is still at a very low level.

Thus, there is an urgent need for the development of a promoter, which promotes the expression of a target protein at high efficiency.

DISCLOSURE OF INVENTION

Accordingly, it is an object of the present invention to isolate a porcine uroplakin II gene promoter, which promotes the bladder-specific expression of a target protein, and also to provide a method capable of producing useful proteins at large amounts using this promoter.

In one embodiment, the present invention provides a porcine uroplakin R gene promoter.

The porcine uroplakin II promoter preferably has a base sequence of SEQ ID NO:1:

```
[SEQ ID NO: 1]:
gggctaggagtggaatcagagctggcctatgccacagcaacgcagaatccaaaccacatctccgacctaca
ccagaccgtcaccataacacaggatccttaacccactgagcaaggtcagggatcaaacccaaatcctcatggatactagt
cgggttcttaacccgctgagccacagtgggcactcctgttttttgtttgtgtcttcgttttttggctgcatctgcagcatacagaa
gttcctgggttaaggattgaacccatgccacagcagcaacccgagccacagcagtgacaacagcctgatccttaactgct
agaccaccagggaacgccccctcaacttttcatgccttggaaacctgagtcagtacaacctgacaatngnttttttttttttttt
ttttttgccttttctagggccacttcccgcggcatgtggagattcgcaggctanaggtctaatcggagctgtagccaccggc
ctacaccagagccatagcaacgagggatccgagccgagtctgcaacctacactacagctcatggcaacaccggatcgtt
aacccactgagcaaggccagggggatcgaaccgcaacctcatggttcctagtcagattcgttaaccactgcaccatgaca
ggaactcccaacctgacaattttatcatttctgcaacctagttgttgagtaatttgaaaaattcccaagatgtcaaggtcagtgt
gatggttaattttatgtgtcaacctgactaggccatgttgcccggatgtggagtcattgttattctggatgttactgtgaagatat
gttttggatgaaattaacatttaaatcagtgggggaaaaaaagaagttctcgttctggtgcatcagaaacaaatccgacta
ggaaacaagcggttgcaggttcgatccctggcctcacttagtggagtcaggatctggcgttgccgtgagctgtggtacag
gtggcagatgcagctcggatctagcattgctgtggctgtggtgtaggccagcagctgtagctctgattaaaccccaagtct
gggaacctccatatgccgtgggtgtggcccgaaaaagcaaaaaataaataaataaataaatttaaaccaggggattttgag
caaagcagattacccataatatgggtgggtctcatcaagttcattgtaggccctagtggaacaaagaccgaccctccacctt
ctccccatgagaaggaaagaattctgccaaaagaccgccttnggacntaaactgcaactctttcctgagtttccagcatgtt
ggcctcccccatcagacttttggacttgccaagcctccgcaattgcatgagccaattccttaaaataaatccgtctatatatac
acatcctgttggttctgtttctccagagaaccctgactaacgcagtctgcaccctgaagaccagtggtccccacactcagc
tgggtgtcacctccaaacactcagccttcctcaaggctctttctagctgtgtcctcctctccccacaacagctgtttcaaactc
tcacccctcttcagggcgcaatcccttctcctccctgagtttcctacttcccagagaaagcagagaccttcaggagtgtgct
gccttaacttacttccttcatccctcagccttgcaaaagtataagctttctctgcaccactgccccattcttctctctgcagacag
ggtcattcctaaagccaaacgctaatgcctccacctctgatctgagtcccatcttttccctcctccagaagcttcctcataaatt
ctaccccctttttcttccttatctttatctttgaaaacaaaatggaagacagccttcccgttgtggtgcagcggaaacagtggtg
ccttggaagcgctgggacgcaggttcgaccctggcccagcatagtaggttaaggatccagtgttgccacagttttggctt
agattgaaactgcagctcagatctggtccctggcctgggaacttcatacgccacaggacggcccaaaaagaaaagaaag
aaaaaataaaaaacaaaacagaaaagcctttcctgtaccccaattccctccagttatctctctctttccctcccagccaag
ctctgcaaagagcggtctgcacagttctaactctacctcctcccagttggccctggactttctcagtctggcttctacccccct
cacccgtaggaatctgctctgaaggacacgcaccccctcacgatccttggcccagggacatttttttgtaccagcctttcaatc
ctgaccttcatatcatccgacacctccttttgtgaaacctccatccactttctcctggttcccctcctaagacccattccgcctt
cttcagcccctccctccatctgtccttagatgccgcatttcctagtatcctgtcctgcgcggnctcgtccttcccttccacaa
ctctcttcaaggactcttttctccatgtgcgattttgcccatggccaccttccctctctcttaaccagacttcccccggtgctcc
agactcatagactcaattatgaaaacatagttttcatctgatttgcccaagatatttgcattagttattactgtataacagcttatc
ccccaatttagtggcttataaaataaacacttattctgagaatcagaaacctaggcaggacatagtgggtctcatgaagtt
gcactgaaaatgtcccctgggctaatcatacggaggactgaccagggctggaggatctgttccaagctcattcattcaca
tggccgtaggttggagacagctcttctctggatcttggcaggagcctcaattccttgtcacgtggacctcccccttggagggg
gtcccatgtcctccatggtgagtaatccatgagagcaaggtggaaggtgccatgccatttaggacctagcctcaggaggg
```

-continued

```
acctacgtcacttctgttgtagtctgttggccacacagactaaccctgacacaatgcacccatccatgacctgctgccagtc
cattctccacactgtttccagaatgatatttacataagtaaaactcctcaaaggcttttgagattttttttcccattatagttgattta
taacctcagaggcttttgttttcttcagcataaaaaccaagttccttaacatagcatgtaacccactggccaccctgccagtg
gctagaactctcaccatgtccatccttgaatactgctttctagccaagagctattgtttgcagttcccagaatgtgtcgggata
actcacatctctgagcctttttcatgtgctgttccctcactttggaatatcccctttccatttaggaaggctaatgtccattcattntc
caaaactcagaagcaaatttttttttttttttttttttttttttttgcttttttagggcgaactctcagcatatggaggttcccaggtta
gccatcaaattggaattgtagctgctggcctacaccacagccatagcaacaccagacccaagtcacatctgcaacctacat
cacagatcatggcaatactggatccttaacccactgagtgagcccagggatcaaacacaaattctcatggatactcgccag
gttcattaccactgagccacaacaggaactcctctccttttttatggtcacacctgcagcatatggaagttcctgggccaggg
attgaatctgagtggcagctgtgacaatgccgtatcctttaattcactgtgctgggctgaggggntaaantgcccctcctaa
aaaacctgagctgctgcagttggattcttaatccactgcaccacaagggggaaggtcaagaactgtcttgccatctctgtat
cttatcacctagcatagtacccaccatagagaagttgctcaacaaatgtttactgaatgaataaatgcatgagctggagttcc
cattgcggctcagcagtaacaaacctgactagcattcataagaacttgggttcgatccctagcctcagtgggttaaggatgc
agcattgctgtgagctgtggtgtaggtcgcagacgacactcagatcccacattgctgtcactgtggcgcaggccggcctct
gtagctctgattcgactcctagcctgggaacgtccatatgccacaggtgaggccctaaaaagaaataaataagcaagcaa
gtaagcaagcaggcagtttcttggtgccttgtaccccgtggcctgtgtggtatacaagtaacagctgatccatgtctcagtc
atgtttccccctcagactacctttcctgccccatctctccctttgacataattggaaaaacaatcagaatttgtcccactacc
tttcttgctagctctgtggccttgggaaagctatttattgcctctgagcctctaattttcatctgcaccaaggattaataaaaagg
agaggataagatgaattacttatattaatatttattgaaccagatactgtgctaggcactcttaaataaattagcttgagtgata
gtcatagtatcctggtgagacagatttttttttttccttttatggttgcacgtgcaacatatggaagttcctgggctggggtcgaat
tggagctgcaggtgcttgcctatgccacagccatggcaacatcatatacaaaccgcacctgtgacctacaccacagattgc
agcaacgctggatccttcacccaaggagcaaggccaggaatcaaatgtgcaatcctatgtccggttttttaac
ccgctgagccacaccaggaactccatggcgagacagattttatactctgtctacagaagaggaaagtgaagctcagaatg
gttaggtaggtaacttggccaagatcaaaaaattcaaagaagatttggggcaagtggtgatatcatggcagcattagaaaa
aataaagaagcatccacttgttttccaacactgaacaactgagattttcttactctcacagcttttttccagcttcatatccaagga
cagacgctctgccattttcccatcagaccaatattttgctgaacactgcacctttactttttaggtccaagtcaccagggttttcc
cagtttgctcctacagattctgacactatctccacattttttttgccactttttattttaaagcattttttatacctgtcataccttgctaga
taaatgggaaggaatgaatcttcccatttataggtgagaaaattgaggttcaaagtgactcaccaaaagtcatatagcatca
ctcctcaacaggaggacagcagtccccaccagagggtaacatgtccatggagcctagtggacacattttttctaactgactg
ggaagcagcagagtggtattgtgaaggggaatcataggtatatcaaacagacttaggttctgatccgagctattctgcttg
caaacaaccatagttcaattttaaaaaaaaaaaagaaagaaagaaagaaagaaaggagccccccatcctggtgcagtggaa
acaaattcaactaggaactgtgaggttgtgggttcgatccctggccttgctcagtgggttaaggatctggcgttgccatgag
ccgtggtgtaggttgcagactcaactcagatctggcgttgctgtgactgtggctgtgatgtaggctggcagctgtaactccg
gttagacccagcctgggaaccctccatatgcaacctccatatgcgggtgtgcccctaaaaagaaaaaaaaaaaaa
aagaggaattcccttatggctcagcaggttaaggatctggtattgtcactgctgtggctctagttacagccatagtgcaggtt
caatccctggcccaggaacgtctgcatcccacaggtgtggccaaaaagaaagaaaggaaggagttctgttgtggcaca
ataggattggcaacatcttaggagtactgggacacaggttcaatccctggcccagcacagtgggtaaggagccagtgttg
ctggtcaaaaaagaaaagaaaaagtaccatagttagagtaaatctgttttaggagctattctttggggcagaacagagagat
caggagctccttgagagcagaaacttaccttttacatccctcgtgcctagcacggttctaggggcatacctggtatttaataaa
tatagccaactggataggggattggaaggaaagagcaggggagggaacttgagtgagttgaaaaattgagaatccaaa
ggggagacagcctagaaagagtaggtccaagaaagagatcccaggcatttgtggcctggttccctttttccaagccatg
aggaaatcctcagaggaacagagtgctgtggctttaaatgacttcagcgttgtcaatgaatctgctcggctaaaagagttat
cctcttgctccttcgcttgtcctcccctcctctcagctccccaaaccctttctcggctgctgtgatgggataattagatgcgag
agctcagcacagatgatgctccagttgcctagcaacatggtttccatggagaccgcaaagcacagcctccagagcag
ccagtgagcagctcggcagggcagggagaagacgcaactctcagctcctccagaaacctggggagggccaggagtg
gggaagaagggggggatcggagggcttaaaggcacaggccctcttatcctcttaaaatctggtcagagctctgccctc
ccctcccctactctgtcccactcataatttcagatggagttgggggcttaggagtggaccaacaacctaccctgcaata
aacccaaccttcttttctgcttctggttttgtggctgaaaatggnaaaagaaatctcccaagtgcaagtgtaaacancntcctg
ggttggcaatgggatctgaagagtactaagatccctcagacctggaattccaccatttagtcttccctctctccaaagttctc
aatgtgcaaaagatcctctttcagtttgcagagcaatgataggatcttctaaaaggagacaaaagccaaggtgcaggaaaa
ataagaattcagttcttcacccaaaggcagcctgtcctgggagacaggggtgaaacacttggtcctgatctccatcagaga
tccagagtgtgtgtgtttgttgctggggagggggacacaatatagagcatctggtgactcaaagtatgtgcctcccagagt
agcatcaatcaatgttacctggaagcttgttagaaatgcagaatttcaggcttcacctcagacccactgaatcagaaactgc
atcttaacaagatccctcatgattcatacgcacattaaatttggagaagcgctgacctgagaccctcctcctctctgcttggg
cccatagttctaccttttattgtcacctcgtctcacctcgtgctcataccccaggcttgagcctccccttcccccatggggaa
aggacacaaggccaccagcccctcacttccctaccaggaccctggccctcctctgggactggagaaggacaaagagga
cccctctgtggaggtctacgacctctcctgaccaagtagtccactcaccacaagtggctctacctctctgagtctcagtttc
cacatccacaaaggtggccaatgctatctgccacccagaatggctgtgagggtggagcaggcaaagcctctgtgccat
cagagaaattgtgtctcttttttcattttctccccagtgggtttcttttctcgtctttattctttttttttttttttttttttcctgtctgttg
tattttttagggccgtgcctgtggcatacggaagttcccagggtaggggtccaatgggagctgtagcccgggcctacgccacagcca
cagcaatgtgggatctgagccacgtctgcaacctacaccacagctcacggcaacaccagatccttaacccactgagcaa
ggccagggatcgagcccacgtcctcatggatgctagttgggttcgttaaccgctgagccatgatgataactcctctttctatt
ctttagtcacaaacagtcaacaaaggttgctgaccaaggctgatcgtgcccaccccccagccccccagactgggccagt
gcccacccctgggtctctctggaaatcctgcccagcatcaattggctccactctccaggaggatgggaagccctgtggc
ccctgggactcacacccctctgcatctcccagagtgcaggacctggtcttcaggagacaccaagaactggctccccgg
ctctgctgccccaccccctactaccagtttctctcccattcctgcccagtccaggcccctggggttactctcctctctctgt
acaccagtgcaacctcagaacctgcttccctcctgggaacaccactaccacgtgggagaagggggtcgtctaggggttg
ggccccagatacacttgtaagcaggaacacacgagccctttcacatgtgggtgtcccggaagaaggggtttttccacccc
cgctttagtcaccctgccctctgcagctgcctgagccaccaagacccagccaaggtctcctgccttctggcctgagggc
cagctccccatcctgaaaacctgtctgggggcctcccctgaggctgtagggcccaaggcctccctgaggctgtaggg
cccaaggggcaggttgaacaggattcccctctggcccctcctaccccaggacaaaaccagagcccaggacagggc
ctcacttgcctcaggaaaccacagcttgccagcacccagcccagcaccagcccagct
```

Moreover, the porcine uroplakin II promoter of the present invention may be one selected from functional equivalents which have one or more disruption, deletion, insertion, point, substitution, nonsense, misense, polymorphism or rearrangement mutation occurred in the base sequence of SEQ ID NO: 1.

In another embodiment, the present invention provides an expression vector containing all or parts of the promoter.

The expression vector of the present invention preferably contains the promoter and also a base sequence coding for a target protein at the 3'-end of the promoter.

In another embodiment, the present invention provides an animal transformed with a fertilized ovum into which the expression vector was introduced.

In still another embodiment, the present invention provides a method for the mass production of useful proteins, which comprises collecting urine from the transgenic animal, and isolating and purifying the target proteins expressed in the urine.

The promoter of the present invention is located at the 5'-end of a porcine uroplakin II gene and regulates the expression of the porcine uroplakin II gene.

The promoter of the present invention can be isolated by screening a porcine genomic library in the following manner.

In order to obtain parts of the base sequence of the porcine uroplakin II gene to be used as a screening probe, the uroplakin II base sequences of other animals with known base sequences are compared to each other and a primer set (forward primer: SEQ ID NO: 2, and reverse primer: SEQ ID NO: 3) is constructed with reference to portions that are well conserved between the species. Then, RT-PCR is performed with the primer set, using the total RNA of the porcine bladder as a template.

After parts of the uroplakin II fragment are obtained through the RT-PCR reaction, a porcine genomic library is screened using the obtained parts as probes. As shown in FIG. 2, the probes used in the present invention are two probes consisting of probe A containing a portion of exons 2-5 of the uroplakin II gene, and probe B containing a portion of exons 1-2 of the uroplakin II gene.

As shown in FIG. 2, the library screening gives clones containing the uroplakin II gene or promoter. The base sequence of the promoter is finally determined by the comparison between the base sequences of the clones, thereby obtaining the complete base sequence of the porcine uroplakin II promoter.

The promoter thus obtained has a total size of 8847 bp, shows high G+C content, a characteristic of a housekeeping gene, in its base sequence, and contains various Sp1 elements, including AP2 and GATA boxes.

The promoter of the present invention specifically expresses a target protein only in bladder tissue among various porcine tissues. In the case of the porcine uroplakin II gene, it is expressed at 8-14% of total bladder cells, and actively propagated, particularly in an urothelial suprabasal cell, and shows high expression level in an umbrella cell being segmented.

Thus, since the promoter of the present invention induces the bladder-specific expression of protein at high efficiency, the use of the inventive promoter allows the production of an expression vector that expresses a target protein of foreign origin in a bladder-specific manner.

In producing the expression vector of the present invention, the inventive promoter is inserted into the existing vector for protein expression, as a basic backbone, and a base sequence coding for a target protein is inserted into the 3'-end of the promoter, thereby producing the inventive expression vector.

The vector, which can be used as a basic backbone in the production of the inventive expression vector, may be a suitable vector selected from general expression vectors, and its examples include pBluescript SK vectors with various cloning sites, and a retroviral vector, such as pLNCX.

The expression vector of the present invention can express all proteins, which are used as an active ingredient of medical drugs, and examples of such proteins include erythropoietin (EPO), aldosterone, adreno-corticotropin, blood clotting factors, gonado-tropin, insulin, prolactin, and vasopressin.

If necessary, the expression vector of the present invention may additionally contain regulators, such as another promoter, an enhancer, a selective marker, a untranslated region (5'-UTR), 3'-UTR, a polyadenylation signal, a ribosome-binding sequence, a base sequence that can be inserted into a certain site of genome, and an intron, at its suitable locations.

The present invention provides expression vector pUP2/hEPO capable of expressing human EPO under the regulation of the porcine uroplakin II promoter (FIG. 3). The expression vector pUP2/hEPO is a preferred example of the expression vectors containing the uroplakin II promoter.

In the expression vector pUP2/hEPO of the present invention, a pBluescript SK(−) vector is used as a basic backbone, and a human EPO-coding gene (Lin F. K. et al, Proc. Natl. Acad. Sci, USA, Cloning and expression of the human erythropoietin gene, 82:7580-7584, 1985; SEQ ID NO: 4) is fused to the 3' end of the inventive uroplakin II promoter. The expression vector pUP2/hEPO was deposited under the accession number KCTC 10352BP on Oct. 17, 2002 with the Korean Collection for Type Cultures (KCTC), Korean Research Institute of Bioscience and Biotechnology.

If necessary, the expression vector pUP2/hEPO of the present invention may additionally contain a neomycin-resistant gene, an insulator, or a woodchuck hepatitis virus post-transcriptional regulatory element (WPRE), such that the establishment of a transgenic cell line can be easily performed, the expression level of a target protein can be maximized and the stability of expression of the target protein can be ensured.

The neomycin-resistant gene is a gene showing resistance to a G418 reagent used in cell line establishment, and can act as an efficient selective marker in the establishment of an animal cell line, which express protein under the regulation of the UPII promoter. The neomycin-resistant gene has a base sequence of SEQ ID NO: 5:

```
gcggccgcgcgcgtcaggtggcacttttcggggaaatgtgcgcggaaccctatttgtttattttttctaaataca          [SEQ ID NO: 5]
ttcaaatatgtatccgctcatgagacaataaccctgataaatgcttcaataatattgaaaaaggaagagtcctgaggcggaa
agaaccagctgtggaatgtgtgtcagttagggtgtggaaagtccccaggctcccagcaggcagaagtatgcaaagcat
gcatctcaattagtcagcaaccaggtgtggaaagtccccaggctcccagcaggcagaagtatgcaaagcatgcatctc
aattagtcagcaaccatagtcccgcccctaactccgcccatcccgcccctaactccgcccagttccgcccattctccgccc
catggctgactaatttttttttattatgcagaggccgaggccgcctcggcctctgagctattccagaagtagtgaggaggctt
ttttggaggcctaggcttttgcaaagatcgatcaagagacaggatgaggatcgtttcgcatgattgaacaagatggattgca
cgcaggttctccggccgcttgggtggagaggctattcggctatgactgggcacaacagacaatcggctgctctgatgccg
ccgtgttccggctgtcagcgcaggggcgcccggttcttttttgtcaagaccgacctgtccggtgccctgaatgaactgcaag
acgaggcagcgcggctatcgtggctggccacgacgggcgttcttgcgcagctgtgctcgacgttgtcactgaagcgg
gaagggactggctgctattgggcgaagtgccggggcaggatctcctgtcatctcacctttgctcctgccgagaaagtatcc
atcatggctgatgcaatgcggcggctgcatacgcttgatccggctacctgcccattcgaccaccaagcgaaacatcgcat
cgagcgagcacgtactcggatggaagccggtcttgtcgatcaggatgatctggacgaagagcatcaggggctcgcgcc
agccgaactgttcgccaggctcaaggcgagcatgcccgacggcgaggatctcgtcgtgacccatggcgatgcctgcttg
ccgaatatcatggtggaaaatggccgcttttctggattcatcgactgtggccggctgggtgtggcggaccgctatcaggac
```

-continued
```
atagcgttggctacccgtgatattgctgaagagcttggcggcgaatgggctgaccgcttcctcgtgctttacggtatcgccg
ctcccgattcgcagcgcatcgccttctatcgccttcttgacgagttcttctgagcgggactctggggttcgaaatgaccgac
caagcgacgcccaacctgccatcacgagatttcgattccaccgccgccttctatgaaaggttgggcttcggaatcgttttcc
gggacgccggctggatgatcctccagcgcggggatctcatgctggagttcttcgcccaccctaggggaggctaactga
aacacggaaggagacaataccggaaggaacccgcgctatgacggcaataaaaagacagaataaaacgcacggtgttg
ggtcgtttgttcataaacgcggggttcggtcccagggctggcactctgtcgatacccaccgagacccattggggccaa
tacgcccgcgtttcttccttttccccaccccaccccccaagttcgggtgaaggcccagggctcgcagccaacgtcggggc
ggcaggccctgccatagcctcaggttactcatatatactttagattgatttaaaacttcattttaatttaaaaggatctaggtga
agatccttttgataatctcatgaccaaaatcccttaacgtgagttttcgttccactgagcgtccgatcg
```

The insulator is a factor promoting the effect of a regulator adjacent to the promoter and also promoting position-independent expression, and allows a target protein to be stably expressed under the regulation of the UPII promoter. The insulator has a base sequence of SEQ ID NO: 6

Such vectors are produced by inserting the neomycin-resistant gene into the inventive pUP2/hEPO vector, and then either inserting the WPRE into the 3' end of the EPO gene or inserting the insulator into the 5' end of the UPII promoter.

[SEQ ID NO: 6]:
```
tcgactctagagggacagcccccccccaaagcccccagggatgtaattacgtccctccccgctagggca
gcagcgagccgcccgggggctccgctccggtccggcgctcccccgcatcccgagccggcagcgtgcggggacag
cccgggcacggggaaggtggcacgggatcgcttcctctgaacgcttctcgctgctctttgagcctgcagacacctgggg
ggatacggggaaaaagctttaggctgaaagagagatttagaatgacagaatcatagaacggcctgggttgcaaaggagc
acagtgctcatccagatccaaccccctgctatgtgcagggtcatcaaccagcagcccaggctgcccagagccacatcca
gcctggccttgaatgcctgcagggatggggcatccacagcctccttgggcaacctgttcagtgcgtcaccaccctctggg
ggaaaaactgcctcctcatatccaaccccaaacctcccctgtctcagtgtaaagccatccccctttgtcctatcaagggggag
ttgctgtgacattgttggtctggggtgacacatgtttgccaattcagtgcatcacggagaggcagatcttgggatgataaagga
agtgcaggacagcatggacgtgggacatgcaggtgttgagggctctgggacactctccaagtcacagcgttcagaaca
gccttaaggataagaagataggatagaaggacaaagagcaagttaaaacccagcatggagaggagcacaaaaaggcc
acagacactgctggtccctgtgtctgagcctgcatgtttgatggtgtctggatgcaagcagaaggggtggaagagcttgcc
tggagagatacagctgggtcagtaggactgggacaggcagctggagaattgccatgtagatgtttcatacaatcgtcaaat
catgaaggctggaaagcctccaagatcccaagaccaaccccaacccaccaccgtgcccactggccatgtccctcagt
gccacatccccacagttcttcatcacctccagggacggtgacccccccacctccgtgggcagctgtgccactgcagcac
cgctctttggagaaggtaaatcttgctaaatccagcccgaccctcccctggcacaacgtaaggccattatctctcatccaac
tccaggacggagtcagtgaggatggggctctagagggacagcccccccccaaagcccccagggatgtaattacgtccc
tccccgctagggcagcagcgagccgcccggggctccgctccggtccggcgctcccccgcatcccgagccggc
agcgtgcggggacagcccgggcacggggaaggtggcacgggatcgctttcctctgaacgcttctcgctgctctttgagc
ctgcagacacctgggggatacggggaaaaagctttaggctgaaagagagatttagaatgacagaatcatagaacggc
ctgggttgcaaaggagcacagtgctcatccagatccaaccccctgctatgtgcagggtcatcaaccagcagcccaggct
gcccagagccacatccagcctggccttgaatgcctgcagggatggggcatccacagcctccttgggcaacctgttcagt
gcgtcaccaccctctggggaaaaactgcctcctcatatccaacccaaacctcccctgtctcagtgtaaagccattccccct
tgtcctatcaagggggagtttgctgtgacattgttggtctggggtgacacatgtttgccaattcagtgcatcacggagaggc
agatcttgggataaggaagtgcaggacagcatggacgtgggacatgcaggtgttgagggctctgggacactctccaa
gtcacagcgttcagaacagccttaaggataagaagataggatagaaggacaaagagcaagttaaaacccagcatggag
aggagcacaaaaaggccacagacactgctggtccctgtgtctgagcctgcatgtttgatggtgtctggatgcaagcagaa
ggggtccatgtccctcagtgccacatccccacagttcttcatcacctccagggacggtgacccccccacctccgtgggca
gctgtgccactgcagcaccgctctttggagaaggtaaatcttgctaaatccagcccgaccctcccctggcacaacgtaag
gccattatctctcatccaactccaggaacggagtcagtgag
```

The WPRE is a regulator contributing to the stabilization of mRNA so as to increase the synthesis of a target protein, and allows the target protein to be expressed at large amounts under the regulation of the UPII promoter. The WPRE has a base sequence of SEQ D NO: 7:

Examples of an animal, which can be transformed with the expression vector of the present invention, include all animals that urinate, such as porcine, mouse, bovine, poultry, ovine and caprine animals.

```
accaggttctgttcctgttaatcaacctctggattacaaaatttgtgaaagattgactggtattcttaactatgttgct       [SEQ ID NO: 7]
ccttttacgctatgtggatacgctgctttaatgcctttgtatcatgctattgcttcccgtatggctttcattttctcctccttgtata
aatcctggttgctgtctcttttatgaggagttgtggcccgttgtcaggcaacgtggcgtggtgtgcactgtgtttgctgacgcaa
cccccctggttggggcattgccaccacctgtcagctccttttccgggacttttcgctttccccctccctattgccacggcgga
actcatcgccgcctgccttgcccgctgctggacaggggctcggctgttgggcactgacaattccgtggtgttgtcgggga
agctgacgtcctttccatggctgctcgcctgtgttgccacctggattctgcgcgggacgtccttctgctacgtccctttcggcc
ctcaatccagcggaccttccttcccgcggcctgctgccggctctgcggcctcttccgcgtcttcgccttcgccctcagacg
agtcggatctcccctttgggccgcctccccgcctgtttcgcctcgggctcctcgag
```

The present invention provides an I/pUP2/hEPO vector, a pUP2/hEPO(WPRE) vector and an I/pUP2/hEPO(WPRE) vector, as preferred examples of the expression vector which additionally contains the regulators.

A method for the production of a transgenic animal using the expression vector of the present invention is conducted according to the conventional method. Namely, a fertilized ovum is collected from a healthy individual among animals to be transformed, and the inventive expression vector is introduced into the fertilized ovum. Then, a pseudopregnant mouse is obtained using a vasectomized mouse, and the fertilized ovum is implanted into the oviduct of the pseudopregnant mouse as a surrogate mother. Then, transformed individuals among the descendants obtained from the surrogate mother are screened.

Thereafter, urine is collected from the screened individuals confirmed to be transformed, and then a target protein is isolated and purified from the collected urine, thereby producing useful proteins.

In the inventive method for the production of useful proteins, the isolation and purification processes of urine can be performed by the conventional technique, such as filtration or chromatography.

The inventive transgenic animal produced as described above expresses a target protein in a bladder-specific manner, and expresses the target protein in urine at a far higher concentration than the existing method.

For example, a mouse transformed with the expression vector pUP2/hEPO of the present invention shows a high EPO expression level of 0.5-1 mg/ml. Although EPO is a protein that is difficult to express since it causes the early death of an embryo, the inventive animal shows at least 1,000 times higher EPO expression level than the expression level of protein in urine, which is obtained using the existing uroplakin promoter.

Furthermore, the protein produced from the inventive transgenic animal shows a superior physiological activity to that of the same kind of commercially available protein.

For example, EPO obtained from a mouse transformed with the expression vector pUP2/hEPO of the present invention maintains the survival rate of an EPO-dependent hepatocyte cell line at a higher level than that of commercially available EPO.

As a result, the promoter of the present invention, and the expression vector and transonic animal using the promoter, can be advantageously used in the production field of useful proteins that have been difficult to produce at large amounts.

BRIEF DESCRIPTION OF DRAWINGS

FIG. 1 shows the structure of probes used in isolating a porcine uroplakin II promoter of the present invention, and clones isolated by the probe;

FIG. 2 shows the structure of expression vector pUP2/hEPO of the present invention;

FIGS. 3a and 3b show the bladder-specific expression of a porcine uroplakin II mRNA;

FIGS. 4a and 4b show the urothelium-specific expression of a porcine uroplakin II protein;

FIGS. 5a, 5b and 5c show the expression level of a porcine uroplakin II protein in bladder cells and the umbrella cell-specific expression of this protein;

FIGS. 6A and 6B show the bladder-specific expression of EPO mRNA in a mouse transformed with the expression vector pUP2/hEPO of the present invention;

FIGS. 7a and 7b show the expression of an EPO protein in a mouse transformed with the expression vector pUP2/hEPO of the present invention;

FIG. 8 shows the structure of the expression vector I/pUP2/hEPO of present invention;

FIG. 9 shows the structure of the expression vector I/pUP2/hEPO(WPRE) of the present invention;

FIG. 10 shows the structure of the expression vector I/pUP2/hEPO(WPRE) of the present invention;

FIGS. 11a, 11b and 11c show the comparison between the EPO gene expression levels of the inventive expression vectors; and FIGS. 12a and 12b show the comparison between the EPO protein expression levels of the inventive expression vectors.

BEST MODE FOR CARRYING OUT THE INVENTION

The present invention will hereinafter be described in further detail by examples. It should however be borne in mind that the present invention is not limited to or by the examples.

EXAMPLE 1

Isolation of Inventive Porcine Uroplakin II Promoter

In order to isolate the porcine uroplakin II promoter of the present invention, the following test was performed.

1) Preparation of probe by RT-PCR (Reverse Transcriptase-Polymerase Chain Reaction)

Since the base sequence of a porcine uroplakin II gene is not yet known, mouse and bovine uroplakin II cDNAs whose base sequences had been known were compared to each other. With reference to portions that are highly conserved between the two species, a degenerate primer set for use in the amplification of the porcine uroplakin II cDNA was produced. The base sequences of the forward and reverse primers are shown in SEQ ID NOS: 2 and 3, respectively.

Using the primer set, RT reaction was performed on the total RNA of the porcine bladder with a MuMLV reverse transcriptase, and the resulting cDNA was subjected to PCR using a Taq polymerase. The reading of the base sequence of the amplified DNA showed that the amplified DNA is parts of an uroplakin II gene. The amplified DNA was cloned with a pGEM T-easy vector.

In order to produce a probe to be used in the isolation of an uroplakin II promoter, 50 ng of the cloned DNA was boiled for 3 minutes, and cooled in ice to denature it. The denatured DNA was added to a reaction buffer containing primer, dNTP, $[\alpha\text{-}^{32}P]dCTP$ (3000 Ci/nmol, NEN), and then a Klenow fragment was added to the solution and reacted at 37° C. for 1 hour. The probes thus obtained consist of probe A comprising a portion of exons 2-5 of the uroplakin II gene and probe B comprising a portion of exons 1-2 of the uroplakin II gene (FIG. 1).

Then, the reaction solution was purified using a Sephadex G-50 column, thereby preparing $^{32}P$-labeled DNA probe A and probe B for porcine uroplakin II promoter probing.

2) Library Screening

To isolate the porcine uroplakin II promoter, a porcine genomic library was screened. In this example, the porcine genomic library which had been inserted into a lambda Fix II phage vector (Stratagene) was used.

Host bacteria to be introduced with the library were prepared as follows.

5 ml LB medium containing 0.2% maltose was inoculated with one bacteria colony and cultured at 37° C. overnight. 1% of the culture medium was transferred into 50 ml of a fresh LB medium containing 0.2% maltose and cultured for 2.5 hours. When the absorbance at 600 nm reached about 0.5, the culture solution was centrifuged at 2,500 rpm for 10 minutes. The resulting cell precipitates were suspended in 10 ml of sterilized magnesium sulfate solution to a final concentration of $1\times10^{10}$ cells/ml, and stored at 4° C. until test.

For titration, the library was serially diluted in SM solution at various concentrations. A plate containing solid LB medium was warmed in a 37° C. incubator, and top agar was dissolved and put in a water bath kept at 48° C. 10 μl of each of the phage solutions diluted at various concentrations was mixed with 100 μl of the above prepared host bacteria, and the host bacteria were infected with the phage at 37° C.

The host bacteria infected with the phage were added to the top agar, well shaken, and then poured on the above-prepared LB medium. After 15 minutes, the plate was turned upside down and cultured in a 37° C. incubator overnight On the medium of the plate cultured overnight, plaques indicating that the phage dissolved the host bacteria after reproducing library DNA in the host bacteria were formed, and for use in a subsequent step, the plate was cooled at 4° C. for at least one hour.

NC filters with serial numbers were provided, and the above-prepared library DNA plate was covered with the filters in such a manner that the middle portion of the filters was first contacted. The filters were pricked with a needle in a vertical direction to the filter so as to mark a position, and one minute later, the filters were carefully separated from the medium.

Each of the filters was successively immersed in denaturation solution, neutralization solution and 2×SSC solution for one minute each solution, and then, placed in an oven at 80° C. for 2 hours such that the transferred library DNA was completely immobilized on the filter.

Each of the immobilized filters was floated on 2×SSC solution to wet it, and then prehybridized in a petri dish containing prehybridization solution with slow shaking at 68° C. for 1 hour. After the prehybridization, each of the filters was added with the probes prepared in the part 1) of Example 1, and hybridized with slow shaking at 68° C. for 18 hours. After the hybridization, the process of immersing the filters in 2×SSC solution containing 0.1% SDS and washing the filters with shaking at 65° C. for 10 minutes was repeated two times. After the washing, the filters were dried in air and subjected to autoradiography.

By the comparison between the autoradiographic result and the plate, a plaque showing a positive sign was selected. The plaque was placed in 500 μl SM buffer solution, and one drop of chloroform was added to and well mixed with the solution, and the mixture was stored at 4° C. Such a screening process was repeated three times, and clones showing a positive sign were finally obtained. DNA contained in each of the clones was purified using a Qiagen lambda mini kit.

The reading of the DNA base sequence was performed using an ABI 377 DNA sequencer (Applied Biosystem), the results of the sequence reading was processed using a CAP2 sequence assembly system, sequence comparison was performed using BLAST, SMART, PROSITE and the like, and motif analysis was conducted using a Clustal W program.

As a result, when the screening was performed with the probe A, clones 1 and 2 as shown in FIG. 1 were obtained. When the probe B was used in the screening, clones and 3 and 4 as shown in FIG. 1 were obtained. Since each of such clones contained a porcine uroplakin II promoter or a structural gene at the 3' end, the comparison between the clones provided the complete base sequence of the porcine uroplakin II promoter.

The porcine uroplakin II promoter of the present invention has a total size of 8874 bp, and its base sequence is shown in SEQ D NO: 1.

3) Examination of expression pattern of protein which is expressed under regulation of inventive promoter In order to examine the expression pattern of a protein, which is expressed under the regulation of the inventive promoter, the expression of porcine uroplakin II was examined as follows.

3-1) Examination of bladder-specific expression of protein which is expressed under regulation of inventive promoter In order to examine if a protein, which is expressed under the regulation of the inventive promoter, is expressed in a bladder-specific manner, Northern analysis was performed.

The porcine uroplakin II cDNA obtained in the part 2) of Example 1 was used as a probe, and at the same time, a probe for actin which is expressed in all tissues at a constant level was provided as a control group. In order to confirm the expression of the porcine uroplakin II mRNA in various porcine body tissues using the probes, total RNA for tissues including the bladder, the heart, the liver, the lungs, the womb and the spleen was subjected to electrophoresis as follows.

0.7 g of agarose was placed in a 250 ml Erlenmeyer flask, added with 58 ml of distilled water, completely dissolved in an electronic rang, and then cooled in a water bath kept at 60° C. When the temperature of the agarose gel was adjusted to 60° C., 7 ml of 10× running buffer was carefully added with shaking, and 11.9 ml of formaldehyde was further added to prepare 1× formaldehyde running gel solution. This solution was placed in a preset electrophoretic system and left to stand for about 20 minutes to produce gel.

6 μl RNA, 2.5 μl 10× running buffer, 4 μl formaldehyde, and 12.5 μl formamide were well mixed in a microcentrifuge tube, and heated at 65° C. for 5 minutes, and then cooled in ice. 2.5 μl gel-loading buffer was added to and well mixed with the sample, and loaded on gel, which had been pre-electrophoresed at 5 V for about 5 minutes. The resulting substance was electrophoresed in 1× running buffer at 120 V/cm. After the electrophoresis, the gel was placed in 0.05 N sodium hydroxide solution for about 10 minutes, so as to partially cut RNA such that an efficiency in a subsequent transfer process is enhanced.

The gel was placed in 0.1 M Tris solution (pH 7.5) for 30 minutes, and in 20×SSC solution (3M sodium chloride, 0.3M sodium-citrate, pH 7.3) for about 30 minutes, and then RNA was transferred to the gel using a positively charged membrane. For RNA immobilization, the transferred membrane was left to stand at 80° C. for 2 hours.

The membrane was placed in a vinyl bag in which hybridization solution was contained at a minimum volume at which the membrane can be completely submerged. Next, the bag was stored in a 68° C. shaking incubator for at least one hour. Then, the solution was drawn out, replaced by 15 ml of a hybridization solution containing the probe, and left to stand in 68° C. shaking incubator overnight.

After the hybridization, the membrane was washed with washing solution 1 (2×SSC, 0.1% SDS) at room temperature for 30 minutes while replacing the washing solution, and then, washed with washing solution 2 (0.2×SSC, 0.1% SDS) at 55° C. for 30 minutes while replacing the washing solution 2. After the membrane was completely dried at room temperature, it was subjected to autoradiography to examine if the porcine uroplakin II mRNA was expressed. The results are shown in FIG. 3.

As shown in FIG. 3*a*, the actin mRNA as an internal control group was uniformly expressed in all the tissues. On the other hand, as shown in FIG. 3*b*, the uroplakin II mRNA which is expressed under the regulation of the inventive promoter was specifically expressed only in the porcine bladder (FIG. 3*b*).

As a result, it can be found that the promoter of the present invention expresses the protein in a bladder-specific manner.

3-2) Examination of urothelium-specific expression of protein which is expressed under the regulation of inventive promoter Meanwhile, in order to examine if the protein which is expressed under the regulation of the inventive promoter is expressed in any cell of bladder tissue, immunohistochemical staining was conducted as follows.

A paraffin fragment of porcine bladder tissue was provided, and maintained in Histoclear solution for about 10 minutes to remove paraffin. The fragment was immersed in aqueous alcohol solution at gradually decreasing concentrations to dehydrate it, and then immersed in methanol containing 3% hydrogen peroxide and 0.05 N hydrochloric acid containing 0.1% pepsin, so as to prevent the fragment being nonspecifically stained.

The fragment was washed two times with TBS buffer (0.05 M Tris, pH 7.4, 0.85% sodium chloride) for 5 minutes, and then, subjected to blocking reaction in TBS which had been diluted with normal equine serum at a ratio of 1:5.

The blocked fragment was immersed overnight in TBS which had been diluted with a primary antibody at a ratio of 1:500. At this time, a polyclonal antibody which can specifically bind to the porcine uroplakin II protein was used as the primary antibody, and one drop of equine serum of an ABC kit was used as a negative control group.

The fragment which had been subjected to the primary antibody reaction was washed two times with TBS for five minutes each time to remove an excess of the antibody, and then reacted with a biotin-attached secondary antibody for 30 minutes. Thereafter, the fragment was washed three times with TBS for 5 minutes, followed by reaction with an ABC reagent for 30 minutes. The fragment was washed with TBS again, rinsed with PBS containing 1% Triton-X 100 for 30 seconds, and then reacted with 0.05M Tris buffer (pH 7.6) containing 0.5% diaminobenzidine (DAB) and 0.01% hydrogen peroxide, to develop color.

After the color development reaction, the fragment was washed with water, mounted on an optical microscope, and observed for its developed portions. The results are shown in FIG. 4.

As shown in FIG. 4a, the control group did not show any positive sign. However, as shown in FIG. 4b, the reaction of the bladder tissue with the antibody to the uroplakin II protein showed that the promoter of the present invention regulated the uroplakin II protein such that the protein is specifically expressed only in the porcine urothelium, particularly in the cytoplasm of the suprabasal cell.

3-3) Examination of expression level of protein which is expressed under regulation of inventive promoter Since the urothelium cell is known to have lower protein synthesis ability than that of mammary gland where the protein synthesis actively occurs, the actual expression level of the protein which is expressed under the regulation of the inventive promoter was examined by Laser scanning cytometry (hereinafter, referred to as 'LS C') in the following manner.

Porcine bladder tissue was split finely, added to DMEM/F12 medium (Gibco) containing 1 mg/ml collagenase type I (Sigma), 0.51 mg/ml byaluronidase (Sigma) and 50 μg/ml gentamicin, and subjected to cleavage reaction at 37° C. for 1 hour.

After the resulting substance was washed with PBS, bulky masses were filtered out using a 60 μm nylon membrane (Milipore), and the suspended single cells were attached to a Lab-Tek chamber slide (Nunc) coated with 0.1% gelatin The cells attached to the slide were washed with cold PBS and immobilized in cold methanol for 15 minutes, followed by treatment in 0.1% Triton-X 100 solution for 10 minutes.

The immobilized cells were blocked in 1% BSA-containing PBS solution for one hour and reacted with a 1:100 solution of the uroplakin II polyclonal antibody prepared in the part 3-2) of Example 1 at room temperature for 2 hours.

After washing with PBS, the cells were reacted with a FITC-attached anti-mouse IgG secondary antibody (Cappel Laboratories). At this time, a group reacted with only the secondary antibody was also prepared as a negative control group.

After the cells were washed three times with PBS containing 0.1% Tween-20, they were stained with 50 μg/ml propidium iodide (PI) such that total cell number can be measured. Upon LSC analysis, fluorescent light was emitted with a 488 nm argon laser, fluorescent expression was observed using a 530 nm filter for FITC and a 570 nm filter for PI. The results are shown in FIG. 5. The results of analysis for the negative control group were shown in FIG. 5a, the results for analysis for the cell expressing the uroplakin II among the bladder cells were shown in FIG. 5b, and the results of analysis for the immune phenotype of the bladder cell expressing the uroplakin II were shown in FIG. 5c.

As shown in FIG. 5b, it was found that about 8-14% of the total bladder cells expressed the uroplakin II. As shown in FIG. 5c, it was found that most of the cells were umbrella cells being actively propagated and cleaved. Considering that proteins in urine are generally at a very low level of 5-25 mg/l, the above-mentioned expression level of the uroplakin II is significantly high Also, it is presumed that the use of bladder tissue allows proteins to be isolated and purified at a higher efficiency than the use of mammary gland tissue.

As a result, it can be found that the promoter of the present invention allows a target protein to be expressed in the bladder at excellent efficiency.

EXAMPLE 2

Production of Inventive Expression Vector pUP2/hEPO

Using the inventive promoter isolated in Example 1, a vector which expresses EPO under the regulation of this promoter was produced in the following manner.

A pBluescript SK(−) vector was selected as a basic backbone vector and inserted with the inventive promoter isolated in the part 2) of Example 1. Thereafter, a gene coding for human EPO (SEQ ID NO: 4) was inserted in the 3'-end of the promoter.

The resulting expression vector has a structure as shown in FIG. 2 and will express EPO under the regulation of the uroplakin II promoter of the present invention. This vector was termed "pUP2/hEPO" and deposited under the accession number KCTC 10352BP on Oct. 17, 2002 with the Korean Collection for Type Cultures (KCTC), Korean Research Institute of Bioscience and Biotechnology.

EXAMPLE 3

Production of Fertilized Ovum Introduced with Inventive Expression Vector pUP2/hEPO A fertilized ovum introduced with the inventive expression vector pUP2/hEPO produced in Example 2 was produced as follows.

1) Collection of fertilized ovum

At 3 days before collecting a fertilized ovum, PMSG was administered into the abdominal cavity of a female mouse, and at 5 p.m., after two days, the female mouse was administered with hCG and then cross-fertilized with a male mouse. In the morning the next day of the cross-fertilization, whether a plug had been produced in the female mouse or not was observed to examine if the female mouse became pregnant.

The mouse that has been confirmed to be pregnant was subjected to cervical vertebral dislocation, its abdomen open was cut with surgical scissors, and the connective tissue portion of the womb was separated. The portion between the oviduct and the womb was torn with a pincette, after which the portion between the ovary and the oviduct was cut with scissors. Then, the side of the womb in the portion torn with the pincette was cut and the oviduct was separated.

The separated oviduct was placed in M2 medium and put on an insulator board to prevent its temperature from being reduced. The oviduct ampulla was broken with a 1 ml needle under a microscope, and an embryo was collected. The collected embryo was placed in hyaluronidase solution that had been exposed to room temperature, and it was left to stand until a cumulus oophorus cell was detached.

The resulting solution was washed 2-3 times with M2 medium, centrifuged at 13,000 rpm for 5 minutes and washed 2-3 times with M2 medium again, and a normal fertilized ovum was screened. The screened fertilized ovum was washed 2-3 times in M16 medium coated with paraffin oil, and then, it was transferred and stored in a 37° C. incubator.

2) Microinjection of DNA into fertilized ovum

Using a micromanipulator, the expression vector pUP2/hEPO of the present invention was injected into the fertilized ovum collected as described above.

EXAMPLE 4

Preparation of Transgenic Mouse which Produces Human EPO Under Regulation of Inventive Promoter Using the fertilized ovum produced in Example 3, a transgenic mouse that produces human EPO under the regulation of the inventive promoter was produced in the following manner.

1) Preparation of vasectomized mouse

A vasectomized mouse to be used in making a surrogate mother pseudopregnant was prepared as follows.

A six-week-old ICR mouse was selected and anesthetized, and then the integument being about 1.5 cm apart above the pubic bone was incised about 1 cm along the pubic bone using a pincette and scissors. Standing to the right or left so as to prevent the incision opening being overlapped, the muscularis was incised, and a testicle descended to the scrotum was moved into the abdominal cavity. The testicle, the epididymis and the spermaduct, were separated from each other with a pincette, a membrane around the speraduct was separated with a pincette, and the spermaduct was cut with a heated pincette. After confirming that the spermaduct had been separated, the muscularis was sutured and the mouse was placed in a warmer until it came of the anesthetic.

2) Preparation of pseudopregnant mouse as surrogate mother

Before the test day, an ICR female mouse that had been confirmed as having estrus was cross-fertilized with the vasectomized mouse prepared in the part 1) of Example 3 In the morning on the test day, whether a plug had been produced in the female mouse or not was observed to examine if the female mouse became pseudopregnant.

3) Embryo transfer into oviduct

The fertilized ova prepared in the part 2) of Example 2 were arranged in a line to a micropipette. The integument and muscularis of the anesthetized female mouse as a surrogate mother were slightly incised, and the ovary, the oviduct and the upper portion of the uterine horn were drawn out of the body using a pincette. The ovary was positioned in such a manner that a portion exposed through the ovarian cyst faces upward. Then, adipose tissue was inserted using a styptic device to fix the ovary. Under a stereoscopic microscope, the membrane of the ovarian cyst was removed, after which the oviduct and the ovary were drawn to look for fimbriae. Then, the front tip of the transplantation pipette was inserted 2-3 mm into the oviduct, and the fertilized ova were carefully implanted into the oviduct together with medium. Whether a first bubble, as a marker, of two bubbles in the pipette had been inserted into the oviduct was observed to examine if the fertilized ova were surely implanted into the oviduct.

Descendants were obtained from the surrogate mother mouse. To screen transgenic mice among them, Northern analysis was performed using the exons 1 and 2 of EPO as probes, and the analysis results showed that 12 of 76 mice were transformed.

The expression pattern of an EPO protein for the transgenic mice was examined and the results showed that the EPO protein was expressed in a bladder-specific manner.

EXAMPLE 5

Production of Human EPO from Inventive Transgenic Mouse

1) Examination of expression level of EPO in urine of inventive transgenic mouse To examine the expression level of EPO in the urine of the inventive transgenic mouse, urine was obtained from the transgenic mouse, and filtered and then subjected to HPLC analysis. To examine the protein components of each fraction, electrophoresis and Western analysis were performed and the results are shown in FIG. 7.

As is evident from the electrophoresis results in FIG. 7a and the Western analysis results in FIG. 7b, the urine obtained from the transgenic mouse of the present invention contained a high concentration of EPO.

The concentration of EPO in the urine was calculated to be an expression level of 0.5-1 mg/ml, which is remarkably higher than the protein expression level in milk that can be seen in the existing transgenic animal.

As a result, the transgenic animal prepared using the inventive promoter can produce a target protein in its urine at excellent efficiency.

2) Examination of physiological activity of EPO obtained from inventive transgenic mouse To examine the physiological activity of EPO obtained from the transgenic mouse of the present invention, EPO obtained in the part 1) of Example 3 was added to EPO-dependent hepatocyte cells and cultured. At this time, a control group was added with commercially available EPO. At each of 24, 48 and 72 hours after the culturing, the survival rate of the cells was measured and the results are given in Table 1 below.

TABLE 1

| Culturing time | DMEM/F12 (%) | FBS | FBS + commercial EPO | FBS + inventive EPO |
|---|---|---|---|---|
| 24 | 38.5 ± 6.8 | 54.9 ± 4.3 | 58.2 ± 6.6 | 72.1 ± 4.7 |
| 48 | 21.6 ± 7.4 | 39.9 ± 2.9 | 50.0 ± 2.4 | 60.4 ± 7.5 |
| 72 | 10.0 ± 4.6 | 20.8 ± 11.7 | 39.6 ± 3.8 | 53.9 ± 4.0 |

As shown in Table 1, it was observed that EPO isolated from the urine of the inventive transgenic mouse showed a higher physiological activity than the commercial EPO in all the time zones.

As a result, the use of the transgenic animal prepared using the promoter of the present invention allows the production of a protein having a far superior physiological activity to a protein that can be obtained by the existing method.

EXAMPLE 6

Production of Inventive Expression Vector Containing Regulators, and Examination of its Efficiency 1) Construction of expression vector containing regulators In order to establish a vector system that can maximize EPO production under the regulation of the inventive UPII promoter, a selective marker and regulators were introduced into the pUP2/hEPO vector in the following manner to produce a series of improved vectors.

1-1) Construction of pUPII/hEPO-Neo vector

In order to insert an efficient selective marker into a vector in the establishment of a cell line that can express a protein under the regulation of the UPII promoter, a neomycin-resistant gene was introduced in the following manner so as to produce a pUP2/hEPO-Neo vector.

To obtain the neomycin-resistant gene, PCR reaction was performed using a pEGFP-N1 vector (Clontech) as a template, and a forward primer (SEQ ID NO: 8) and a reverse primer (SEQ ID NO: 9).

```
5'-GCGGCCGCGCGCGTCAGGTGGCAC-3'        (SEQ ID NO: 8)

5'-CGATCGGACGCTCAGTGGAACGAAAACTC-3'   (SEQ ID NO: 9)
```

The resulting 1.9-kb PCR product was inserted into a pGEM T-easy vector and digested with a NotI restriction enzyme, to prepare the neomycin-resistant gene portion to be used in cloning.

The ampicillin-resistance gene site of the inventive pUP2/hEPO vector was removed by digestion with NotI and SalI restriction enzymes, to prepare a vector to be used in cloning.

The neomycin-resistant gene prepared as above described was cloned into to the vector, thereby producing the pUP2/hEPO-Neo vector where the neomycin-resistant gene was inserted into the existing pUP2/hEPO vector.

1-2) Construction of I/pUP2/hEPO Vector

In order to obtain an expression vector which can stably express a protein under the regulation of the UPII promoter, an insulator gene was introduced into a pUP2/hEPO-Neo vector in the following manner so as to produce an I/pUP2/hEPO vector.

To obtain the insulator gene, PCR reaction was performed using a pBC1 vector Invitrogen) containing a chicken B-globin insulator gene, as a template, and a forward primer (SEQ ID NO: 10) and a reverse primer (SEQ ID NO: 11). To increase PCR efficiency, two copies were amplified.

```
    5'-TCGACTCTAGAGGGACAG-3'     (SEQ ID NO: 10)

5'-CTCACTGACTCCGTTCCT-3'     (SEQ ID NO: 11)
```

The resulting 2.4-kb PCR product was inserted into a pGEM T-easy vector and digested with a NotI restriction enzyme, to prepare the insulator gene to be used in cloning.

The insulator gene prepared as described above and the vector of the above part 1-1) were coupled to each other by a NotI site, thereby producing the I/pUP2/hEPO vector (FIG. 8).

1-3) Construction of pUP2/hEPO (WPRE) vector

In order to obtain an expression vector that can express a protein at large amounts under the regulation of the UPII promoter, a WPRE gene was introduced into the pUP2/hEPO-Neo vector in the following so as to produce a pUP2/hEPO (WPRE) vector.

To clone the WPRE gene, PCR reaction was performed using a forward primer (SEQ ID NO: 12) and a reverse primer (SEQ ID NO: 13).

```
5'-ACCAGGTTCTGTTCCTGTTAATCAACCTC-3'(SEQ ID NO: 12)

5'-CTCGAGGAGCCCGAGGCGAAACAGGCG-3'(SEQ ID NO: 13)
```

The resulting 0.6-kb PCR product was inserted into the pGEM T-easy vector and then inserted into the NcoI restriction site of the pUP2/hEPO-Neo produced in the part 1-1) of this Example. The resulting vector was digested with a BspHI restriction enzyme, to prepare the WPRE gene to be used in cloning.

Meanwhile, the backside of the EPO gene of the inventive pUP2/hEPO vector was digested with an NcoI restriction enzyme, to prepare the vector to be used in cloning.

The WPRE gene prepared as described above was cloned into the vector, to produce the pUP2/hEPO (WPRE) vector (FIG. 9).

1-4) Construction of I/pUP2/hEPO (WPRE) vector

In order to produce an expression vector that can satisfy all the maximization of expression level, the stabilization of expression and the establishment of an efficient cell line under the regulation of the UPII promoter, an I/pUP2/hEPO (WPRE) vector was produced in the following manner.

The insulator gene prepared in the part 1-2) of this Example was coupled with the vector of the part 1-3) of this example by a NotI site, thereby producing the I/pUP2/hEPO vector (FIG. 10).

2) Examination of efficiency of inventive expression vectors

The efficiency of the expression vectors produced in Example 6 was examined in the following manner.

2-1) PCR analysis for inventive expression vectors

To examine the expression level of the EPO gene, which is caused by inventive expression vectors, real-time PCR was performed as follows.

The four inventive expression vectors produced in Example 6 were introduced into bladder cell line RT4 using a transfection Kit (Effectene, Qiagen) and then subcultured to establish stable cell lines. Genomic DNA was extracted from each of the resulting cell lines and subjected to PCR to examine if the transfection was properly made.

To examine the expression level of the EPO gene, total RNA was extracted from the four cell lines and subjected to RT-PCR to amplify cDNA. The PCR was performed using the above cDNA as a template, and forward and reverse primers capable of amplifying the exon region of EPO.

To examine the expression level in each of the cell lines, this process was repeated three times using, as a control group, GAPDH that is a house keeping gene which is expressed in cells at a constant level. The test results were statistically processed using a SAS program and shown in FIG. 11 (pUP2=pUP2/hEPO vector; IUP2=I/pUP2/hEPO vector, PW=pUP2/hEPO (WPRE) vector, and IW=I/pUP2/hEPO (WPRE) vector).

As shown in FIG. 11, the inventive expression vectors showed EPO gene expression level that is higher in the order of the pUP2/hEPO vector, the I/pUP2/hEPO vector, the pUP2/hEPO (WPRE) vector, and the I/pUP2/hEPO (WPRE) vector.

Particularly, the I/pUP2/hEPO (WPRE) vector which contains both the WPRE and the insulator showed about 50 times higher expression level than the pUP2/hEPO containing no separate regulators (FIG. 11b).

As a result, the inventive expression vectors, including the I/pUP2/hEPO (WPRE) vector, can be advantageously used for the production of EPO.

2-2) Western Analysis for Inventive Expression Vectors

To examine the expression level of EPO protein caused by the expression vectors of the present invention, Western analysis was performed as follows.

The cell lines which had been established by introducing the respective expression vectors of the present invention in the part 2-1 of Example 6 were placed in a lysis buffer containing NP-40 and sonicated to extract proteins from the cell lines.

Each 40 µl of the proteins were electrophoresed on SDS-PAGE gels, transferred to a PVDF membrane, and then treated with an EPO antibody to examine the expression level of an EPO protein. To quantify the expression level of the EPO protein, this process was repeated two times using an antibody for actin as a control group. The results were statistically processed with a SAS program and shown in FIG. 12 (pUP2=pUP2/hEPO vector, IUP2=I/pUP2/hEPO vector; PW=pUP2/hEPO (WPRE) vector, and IW=I/pUP2/hEPO (WPRE) vector).

As shown in FIG. 12, the expression vectors of the present invention showed the expression level of EPO protein, which is higher in the order of the pUP2/hEPO vector, the I/pUP2/hEPO vector, the pUP2/hEPO (WPRE) vector, and the I/pUP2/hEPO (WPRE) vector.

This result coincides with the results shown in the part 2-1) of Example 6.

As a result, the inventive expression vectors, including the I/pUP2/hEPO (WPRE) vector, can be advantageously used for the production of EPO.

INDUSTRIAL APPLICABILITY

As described above, the promoter of the present invention induces the bladder-specific expression of a target protein, and expresses the target protein in urine at a far higher concentration than the existing method.

The animal, which was transformed with the expression vector consisting of the inventive promoter and the target protein being regulated by the promoter, secretes the target protein in urine at a far higher efficiency than that of the existing transgenic animal. Furthermore, the protein obtained from the transgenic animal of the present invention shows a superior physiological activity to the same kind of the existing protein.

As a result, the promoter of the present invention, and the expression vector and transgenic animal using this promoter, can be advantageously employed in the production field of useful proteins that are medicinally valuable.

What is claimed is:

1. An isolated porcine uroplakin II gene promoter having the base sequence of SEQ ID NO: 1.

2. An expression vector comprising the base sequence of the promoter of claim 1 and a base sequence coding for a target protein at the 3' end of the promoter.

3. The expression vector of claim 2, wherein the target protein is human erythropoietin (EPO).

4. The expression vector of claim 3, which is the expression vector pUP2/hEPO deposited under the accession number KCTC 10352BP.

5. The expression vector of claim 3, which is an I/pUP2/hEPO vector containing the neomycin-resistant gene of SEQ ID NO: 5 as a selective marker, and the insulator of SEQ ID NO: 6 at the 5' end of the UPII promoter.

6. The expression vector of claim 3, which is a pUP2/hEPO (WPRE) vector containing the neomycin-resistant gene of SEQ ID NO: 5 as a selective marker, and the woodchuck hepatitis virus posttranscriptional regulatory element (WPRE) of SEQ ID NO: 7 at the 3' end of the EPO gene.

7. The expression vector of claim 3, which is an I/pUP2/hEPO (WPRE) vector that contains the neomycin-resistant gene of SEQ ID NO: 5 as a selective marker, the insulator of SEQ ID NO: 6 at the 5' end of the UP2 promoter, and an WPRE of SEQ ID NO: 7 at the 3'-end of the EPO gene.

8. A fertilized mouse ovum transfected with the expression vector of claim 3.

9. A fertilized mouse ovum transfected with the expression vector of claim 4.

10. A fertilized mouse ovum transfected with the expression vector of claim 5.

11. A fertilized mouse ovum transfected with the expression vector of claim 6.

12. A fertilized mouse ovum transfected with the expression vector of claim 7.

13. A transgenic mouse obtained by the implantation of the fertilized ovum of claim 8.

14. A transgenic mouse obtained by the implantation of the fertilized ovum of claim 9.

15. A transgenic mouse obtained by the implantation of the fertilized ovum of claim 10.

16. A transgenic mouse obtained by the implantation of the fertilized ovum of claim 11.

17. A transgenic mouse obtained by the implantation of the fertilized ovum of claim 12.

18. A method for producing erythropoietin (EPO), which comprises the steps of:
   implanting a fertilized mouse ovum transfected with the expression vector of claim 3 into a surrogate mother mouse; and
   obtaining transgenic mice from the surrogate mother mouse; and
   isolating and purifying EPO from the urine of at least one of the transgenic mice.

19. A method for producing erythropoietin (EPO), which comprises the steps of:
   implanting fertilized mouse ovum transfected with the expression vector of claim 4 into a surrogate mother mouse; and
   obtaining transgenic mice from the surrogate mother mouse; and
   isolating and purifying EPO from the urine of at least one of the transgenic mice.

20. A method for producing erythropoietin (EPO), which comprises the steps of:
   implanting a fertilized mouse ovum transfected with the expression vector of claim 5 into a surrogate mother mouse; and
   obtaining transgenic mice from the surrogate mother mouse; and
   isolating and purifying EPO from the urine of at least one of the transgenic mice.

21. A method for producing erythropoietin (EPO), which comprises the steps of:
   implanting a fertilized mouse ovum transfected with the expression vector of claim 6 into a surrogate mother mouse; and
   obtaining transgenic mice from the surrogate mother mouse; and
   isolating and purifying EPO from the urine of at least one of the transgenic animals.

22. A method for producing erythropoietin (EPO), which comprises the steps of:
   implanting a fertilized mouse ovum transfected with the expression vector of claim 7 into a surrogate mother mouse; and
   obtaining transgenic mice from the surrogate mother mouse; and
   isolating and purifying EPO from the urine of at least one of the transgenic mice.

* * * * *